United States Patent [19]

Lo et al.

[11] Patent Number: 4,480,100
[45] Date of Patent: Oct. 30, 1984

[54] [2-[(NITROPYRIDINYL)AMINO]PHENYL-]ARYMETHANONES

[75] Inventors: Young S. Lo, Richmond; Chandler R. Taylor, Jr., Mechanicsville, both of Va.

[73] Assignee: A. H. Robins Company, Inc., Richmond, Va.

[21] Appl. No.: 431,997

[22] Filed: Sep. 30, 1982

[51] Int. Cl.³ .................. C07D 213/61; C07D 213/74
[52] U.S. Cl. .................... 546/307; 546/256; 546/261; 546/264; 546/272; 546/281; 546/284; 546/297; 546/283; 424/263; 424/248.5; 424/248.56; 424/250; 544/131; 544/124; 544/405; 260/244.4; 260/243.3
[58] Field of Search ................ 546/307, 297

[56] References Cited
PUBLICATIONS
Ozawa et al. Chem. Abs. 53388v.
Kobayashi et al. Chem. 84:164876a.

Primary Examiner—Jane T. Fan

[57] ABSTRACT

[2-[(Nitropyridinyl)amino]phenyl]arylmethanones as chemical intermediates and/or having antidepressant activity having the formula:

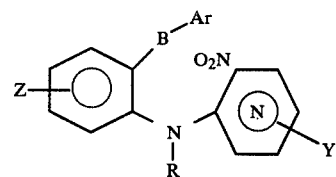

wherein:
B is carbonyl, thioxomethyl, ketal or thioketal,
R is hydrogen or -alk$^1$-Q,
Q is hydrogen, —NR$^1$R$^2$ or halogen
are disclosed in a process for preparing pyrido[1,4]benzodiazepines.

10 Claims, No Drawings

[2-[(NITROPYRIDINYL)AMINO]PHENYL]ARYMETHANONES

BACKGROUND OF INVENTION

1. Field of Invention

The present invention is concerned with a novel process for the preparation of certain pyrido[1,4]benzodiazepines which have antidepressant activity via novel [2-[(nitropyridinyl)amino]phenyl]arylmethanone precursors and the thioxomethyl, ketal or thioketal analogs thereof. Certain of these precursor compounds and derivatives which are part of the invention thereof have antidepressant activity.

2. Description of the Prior Art

Wander, A. in British Pat. No. 907,646 discloses preparation of certain dibenzodiazepines substituted with phenyl radicals on carbon and with alkyl or aminoalkyl radicals on the solitary bridging nitrogen. The method of preparation used by Wander is via cyclodehydration of orthoacyl aminodiphenylamines. Arylmethanones and pyrido compounds are not involved.

Japanese Pat. No. 73/43,520 (C.A. 80: 133501n) discloses preparation of dibenzodiazepines illustratively from 2-aminobenzophenones and ornithine.

[2-[(Aminopyridinyl)amino]phenyl]arylmethanones useful as antidepressant agents or as intermediates in a process for preparing certain pyrido[1,4]benzodiazepines are disclosed in U.S. application Ser. No. 305,080 filed Sept. 24, 1981. The method of preparation in that application involves starting with a haloaminopyridine rather than a halonitropyridine as in the present invention.

SUMMARY AND OBJECTS OF THE INVENTION

The present invention provides a new route to certain pyrido[1,4]benzodiazepines via novel [2-[(nitropyridinyl)amino]phenyl]arylmethanones and analogs having the formula:

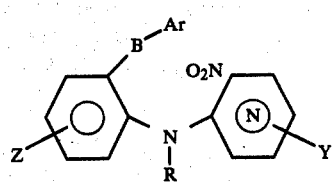

Formula I wherein;

R is selected from hydrogen or —alk$^1$—Q;

Q is selected from the group consisting of hydrogen, —NR$^1$R$^2$ or halogen;

alk$^1$ is a straight or branched hydrocarbon chain containing 1-8 carbons;

B is selected from the group consisting of carbonyl, thioxomethyl, ketal or thioketal;

R$^1$ and R$^2$ are selected from the group consisting of hydrogen, loweralkyl, —C(O)—O—loweralkyl, or R$^1$ and R$^2$ taken together with the adjacent nitrogen atom may form a heterocyclic residue selected from 1-phthalimido, 1-pyrrolidinyl, 1-piperidinyl, 4-morpholinyl, 1-piperazinyl and 4-substituted-1-piperazinyl;

Ar is selected from the group consisting of 2 or 3 thienyl, 2, 3 or 4-pyridinyl, phenyl or phenyl substituted by 1 to 3 radicals selected from halo, loweralkyl, loweralkoxy, trifluoromethyl or nitro which may be the same or different;

Y is selected from the group consisting of hydrogen, or 1-2 radicals selected from loweralkyl, hydroxy or loweralkoxy and may be the same or different;

Z is selected from the group consisting of hydrogen, halogen, loweralkyl, hydroxy, loweralkoxy or nitro;

and the acid addition salts thereof.

In the process for preparation of the pyrido[1,4]benzodiazepines, compounds of Formula I are reduced to [2-[(aminopyridinyl)amino]phenyl]arylmethanones and their thioxomethyl, ketal or thioketal analogs having the general Formula II:

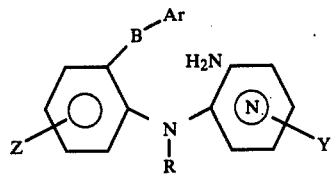

Formula II wherein Ar, B, Y, Z and R have the values given above. The compounds of Formula II wherein B is carbonyl or thioxomethyl have antidepressant activity except when Q is phthalimido, chloro or when Q is NR$^1$R$^2$ with either R$^1$ or R$^2$ being —C(O)—O—loweralkyl.

The compounds of Formula I and their pharmaceutically acceptable acid addition salts wherein B is carbonyl or thioxomethyl generally have antidepressant utility except when R is H or when Q is 1-phthalimido, chloro or when Q is NR$^1$R$^2$ with either R$^1$ or R$^2$ being —C(O)—O—loweralkyl. Compounds represented by these exceptions are chemical intermediates in the process. The compounds of Formula II are disclosed as antidepressants or chemical intermediates in the aforementioned copending application.

The compounds of Formula I and II, except wherein either or both R$^1$ or R$^2$ are hydrogen, are generally chemical intermediates in the preparation of pyrido[1,4]benzodiazepines having the general formula:

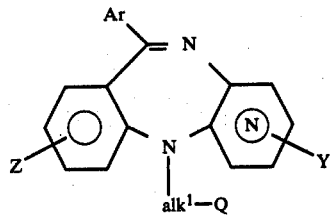

Formula X wherein Ar, Y, Z, alk$^1$ and Q have the values given under Formula I above.

Generally, in the process of this invention [2-[(nitropyridinyl)amino]phenyl]arylmethanones and analogs substituted on the solitary bridging nitrogen with an alkyl (alkylation) or an —alk$^1$NR$^1$R$^2$ radical (aminoalkylation) wherein R$^1$ and R$^2$ are as defined above, excluding hydrogen, are prepared, the nitro radical is reduced to amino. The resulting [2-[(aminopyridinyl)amino]phenyl]arylmethanone cyclizes to pyrido[1,4]benzodiazepine of Formula X.

As will be realized, compounds of Formula I wherein either or both R$^1$ and R$^2$ are hydrogen are not intermediates in the preparation of the pyrido[1,4]benzodiazepines of Formula X, but they can be prepared for antidepressant utility by appropriate conversions of other intermediates as set forth below. It will be further realized that compounds of Formula X wherein R¹ and R² are either singly or both hydrogen can be prepared by similar techniques.

As indicated by the foregoing Formula X, location of the pyrido nitrogen is variable, illustratively as follows in Formulas Xa, Xb, Xc, and Xd all encompassed by Formula X:

The 6-aryl-11H-pyrido[2,3-b][1,4]benzodiazepines encompassed by Formula X have the formula

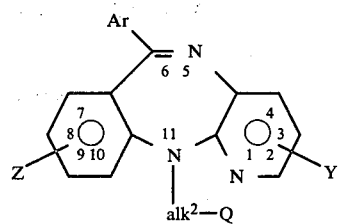

Formula Xa

The 6-aryl-11H-pyrido[3,4-b][1,4]benzodiazepines encompassed by Formual X have the formula

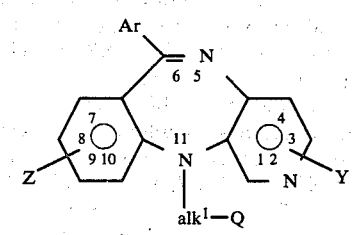

Formula Xb

The 10-aryl-5H-pyrido[4,3-b][1,4]benzodiazepines encompassed by Formula X have the formula

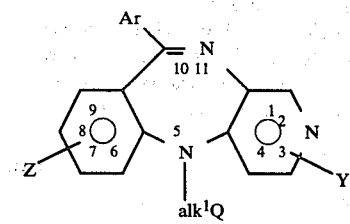

Formula Xc

The 10-aryl-5H-pyrido[3,2-b][1,4]benzodiazepines encompassed by Formula X have the formula

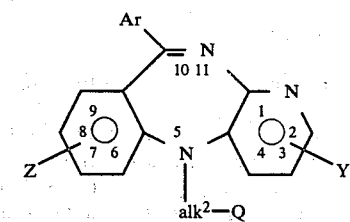

Formula Xd

As will be further recognized by the indefinite position of pyrido nitrogen in Formula I, the [2-[(nitro and aminopyridinyl)amino]phenyl]arylmethanones and their analogs encompassed thereby and useful as antidepressants or in the preparation of the corresponding compounds of Formulas Xa, Xb, Xc, and Xd have varying positions of pyrido nitrogen. The following variations: Iw, Ix, Iy, and Iz encompassed by Formula I covering all positions of the pyrido nitrogen within the scope of this invention in relation to other substituents are as follows:

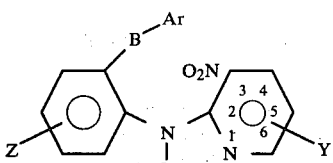

Iw

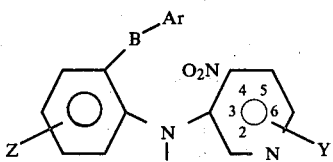

Ix

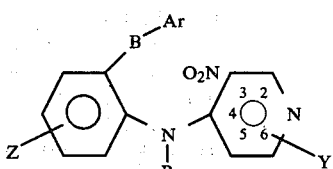

Iy

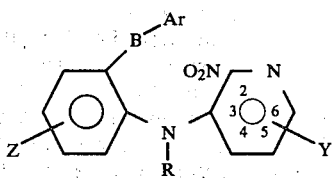

Iz wherein R, B, Z and Ar are as defined under Formula I above.

In the further definition of symbols, the term "loweralkyl" as used herein includes straight or branched chain radicals containing 1–8 carbon atoms as, for example, methyl, ethyl, propyl, isopropyl, n-butyl, isobutyl, tertiary butyl, amyl, isoamyl, n-hexyl, n-heptyl and n-octyl radicals and the like. The "loweralkoxy" radical has the formula "—O—loweralkyl."

The "alk¹" straight or branched connecting hydrocarbon chain containing 1 ∝ 8 carbon atoms is exemplified by methylene (—CH₂—), ethylene (—CH₂CH₂—), propylene (—CH₂CH₂CH₂—),

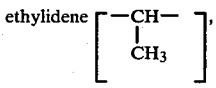

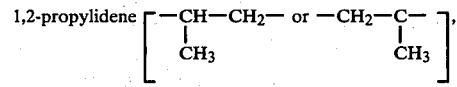

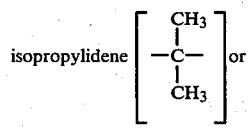

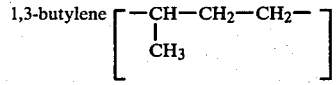

and the like.

The term halogen includes chlorine, bromine, fluorine and iodine, preferably chlorine, bromine and fluorine.

The term "4-substituted-1-piperazinyl" refers to the piperazine radical substituted in the 4-position by loweralkyl or alkoxy carbonyl or any blocking group which may subsequently be removed to give the substituted piperazine radical.

By "acid addition salts" is meant salts formed with the compounds of Formulas I or X which may be prepared by the process of this invention or in the course of the reactions of the process or for the purpose of aiding in the isolation or purification of any compound or in any pharmaceutical preparation. Examples of addition salts of strong acids are those formed with hydrochloric, sulfuric and phosphoric acids and the like. Examples of addition salts of weak acids are those formed with fumaric, maleic, and oxalic acids and the like. The pharmaceutically acceptable acid addition salts are those formed with acids which are suitable for human administration.

Salts of compounds of Formulas I, II and X may be converted to the free base by partitioning between a solvent such as methylene chloride and an aqueous base such as sodium hydroxide and evaporating the solvent layer in vacuo.

For the purpose of establishing antidepressant activity of the compounds of Formulas I, II and X, the procedure given by Engelhardt, E. L. et al, J. Med. Chem. 11 (2): 325 (1968) was followed. The compound in amount of 20 mg/kg was administered to five adult mice (ICR-DUB strain) intraperitoneally 30 min. prior to the administration of a ptotic dose (32 mg/kg, IP) of tetrabenazine (as the methane sulfonate salt). Thirty minutes later, the presence or absence of complete eyelid closure (ptosis) is assessed in each animal. An $ED_{50}$ (Median Effective Dose) may be established for any given compound in blocking tetrabenazine induced ptosis in mice following the procedure given by Litchfield, et al., J. Pharmacol. Ex. Therap. 96: 99-113 (1949).

It is therefore an object of the present invention to provide a novel process for the preparation of pyrido [1,4]benzodiazepines substituted by alkyl and aminoalkyl radicals on the solitary bridging nitrogen.

Another object is to provide novel [2-[(nitropyridinyl)amino]phenyl]arylmethanones and analogs of Formula I, methods of preparation and use as antidepressants or as intermediates in the preparation of [2-[(aminopyridinyl)amino]phenyl]arylmethanones and analogs and pyrido[1,4]benzodiazepines both of which have anti-depressant activity.

Additional objects and advantages of the present invention will be apparent to one skilled in the art and still others will become apparent from the following description of the best mode of carrying out the present invention and the appended claims.

DETAILED DESCRIPTION OF THE INVENTION

The present invention encompasses the process for preparing the pyrido[1,4]benzodiazepines (Formula X), the [2-[(nitropyridinyl)amino]phenyl]arylmethanones and analogs (Formula I) as composition of matter and use thereof as antidepressant agents as well as any portion of the process as it pertains to the preparation of the intermediates (Formulas I and II).

The novel process of this invention for preparing the pyrido[1,4]benzodiazepines comprises the steps of Step (1) reacting a 2-aminophenyl-arylmethanone or analog having the formula:

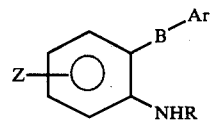
IV with a halo-nitropyridine having the formula:

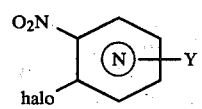
III to give a [2-[(nitropyridinyl)amino]phenyl]arylmethanone or analog having the formula:

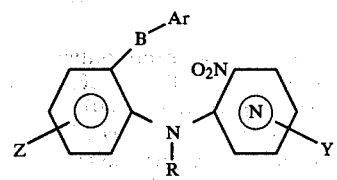
Ic wherein R is selected from hydrogen, methyl or ethyl; and Ar, B, Y and Z are as defined above under Formula I;

Step (2) reacting a compound obtained in step 1 wherein R is hydrogen with a reagent having the formula:

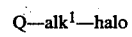

Q—alk$^1$—halo to give a compound having the formula:

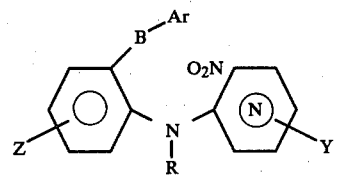
Ib wherein R is —alk$^1$—Q; and Ar, B, Y, Z, alk$^1$ and Q are as defined under formula I above, except neither R$^1$ nor R$^2$ are hydrogen;

Step (3) reducing the nitro group of a compound prepared in steps 1 and 2 to give a compound selected from those having the formula:

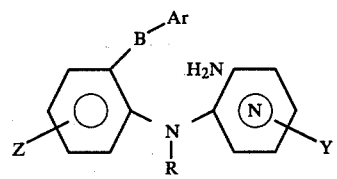
Ia wherein Ar, B, Y, Z, R, alk$^1$ and Q are as defined under Formula I, except neither R$^1$ nor R$^2$ are hydrogen;

Step (4) cyclizing a compound obtained in step 3 to give a compound having the formula:

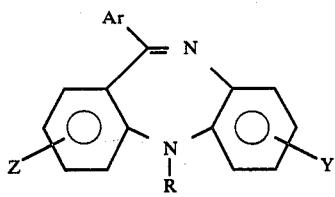

wherein Ar, Y, Z and R are as defined under Formula I, except neither $R^1$ nor $R^2$ are hydrogen.

DESCRIPTION OF COMPOUND PREPARATION

Reaction sequence by equation showing preparation of compounds of the invention (Formula I) and utility thereof in preparation of the corresponding [2-[(aminopyridinyl)amino]phenyl]arylmethanones (Formula II) and the pyrido [1,4]benzodiazepines are given in Charts I to V.

Preparation of [2-[(nitropyridinyl)amino]phenyl]arylmethanones and analogs.

Generally, a mixture of halonitropyridine and the aminobenzophenone (or analog) (R=H, $CH_3$ or $C_2H_5$) are heated together at temperatures of 110° to 160° C. for a period of time to effect reaction, usually ½ hr to 4 hrs. The methanones (and analogs) are isolated by cooling the melt and adding a suitable solvent and partitioning between the solvent and aqueous base followed by washing and drying the solvent layer and evaporating and recrystallizing from a suitable solvent. Compounds of Formula I wherein —$alk^1$—Q is a methyl or ethyl radical are finished at this stage. Compounds of Formula I wherein R is H are further reacted with a reagent of the formula Q—$alk^1$—halo as defined in Chart I, preferably by heating in admixture with an aqueous alkali metal base suitably sodium hydroxide; an organic solvent suitably methylene chloride; and a phase transfer catalyst, suitably tricaprylyl ammonium chloride, for a period of time sufficient to give good reaction as indicated by mass spectrascopy data. Crude product may be obtained by carefully adjusting the pH from strongly basic to slightly basic and thereafter extracting with a suitable solvent such as methylene chloride and evaporating the solvent.

Preparation of [2-[(aminopyridinyl)amino]phenyl]arylmethanones and analogs

The nitro compounds are reduced by any one of several methods; for example with
(a) palladium/C and hydrogen
(b) iron powder and acetic acid
(c) zinc powder and base These intermediate products are difficult to isolate from the reaction mix and are more suitably utilized by allowing cyclization directly to the pyrido[1,4]benzodiazepine without isolation and this is therefore a preferred procedure.

The primary amines of Formula I wherein $R^1$ and $R^2$ are both hydrogen are prepared from the compounds also of Formulas I and II wherein the bridging nitrogen is substituted by —$alk^1$—(1-phthalimido) as shown in Chart II by reacting with hydrazine hydrate utilizing the method of Org. Syn. Coll. Vol. III, pp 151–153. Generally, after sufficient reflux time, aqueous acid is added and the mixture is filtered. The primary —alk-$^1$—amines are isolated from suitable solvents selectable by trial and error. Hydrochlorides are preferred salts in the isolation step.

The $alk^1$—monoalkylamines of Formula I; e.g. $R^1$=methyl, $R^2$=hydrogen, may be prepared as shown in Chart II by reacting the primary —$alk^1$—$NH_2$ derivatives with refluxing triethyl orthoformate for a period of time sufficient to form the methanimidic acid ester which is then reacted with sodium borohydride. The unreacted borohydride is decomposed with water and the product extracted out with a suitable solvent such as ethyl acetate and may be purified by column chromatography and partitioning with solvent and aqueous base. Hydrochlorides are preferred salts in the isolation step.

—$Alk^1$—monomethylamines of Formula I may also be prepared by reaction of the primary amine with ethyl chloroformate and thereafter reducing with lithium aluminum hydride as exemplified in Chart II. Alternative reductions when B is varied are also shown in Chart II.

A further more generalized alternative for introduction of —$alk^1$—monoloweralkyl amine radicals is via hydrolysis of the radical

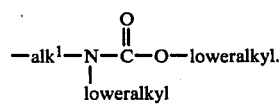

See Charts I and IV.

An alternative method of preparing compounds of Formula I wherein Q is —$NR^1R^2$ is illustrated in Chart III.

Compounds of Formula I wherein the —$NR^1R^2$ moiety is unsubstituted 1-piperazinyl are obtained by hydrolyzing compounds of Formula I wherein —$NR^1R^2$ is piperazino substituted in the 4-position by an alkyl carbonyl such as t-butoxycarbonyl.

CHART I

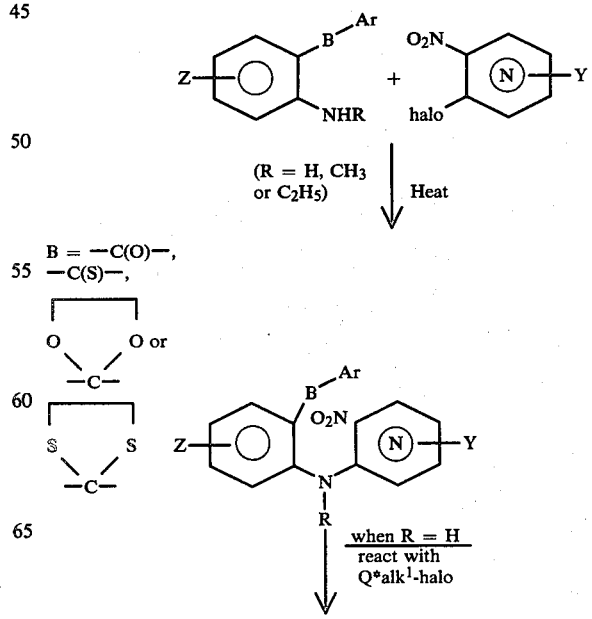

-continued
CHART I
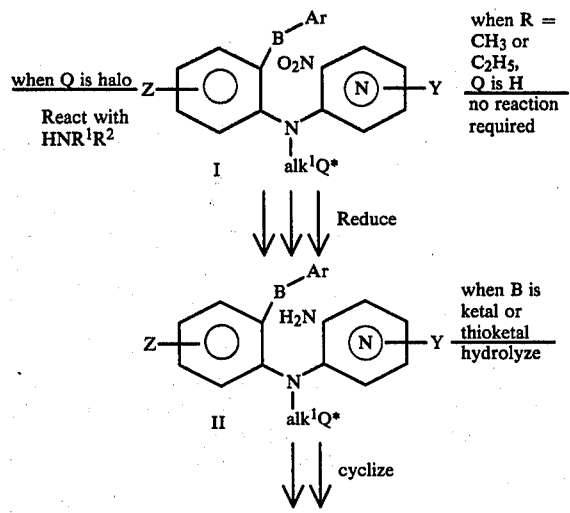
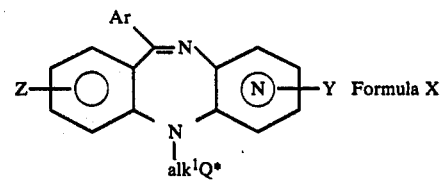
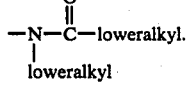
Q* is selected from the group consisting of hydrogen, halo, —N(loweralkyl)$_2$, 1-pyrrolidinyl, 1-piperidinyl, 4-substituted piperazin-1-yl, 4-morpholinyl, 1-phthalimido or
—N(loweralkyl)—C(O)—loweralkyl.
CHART II
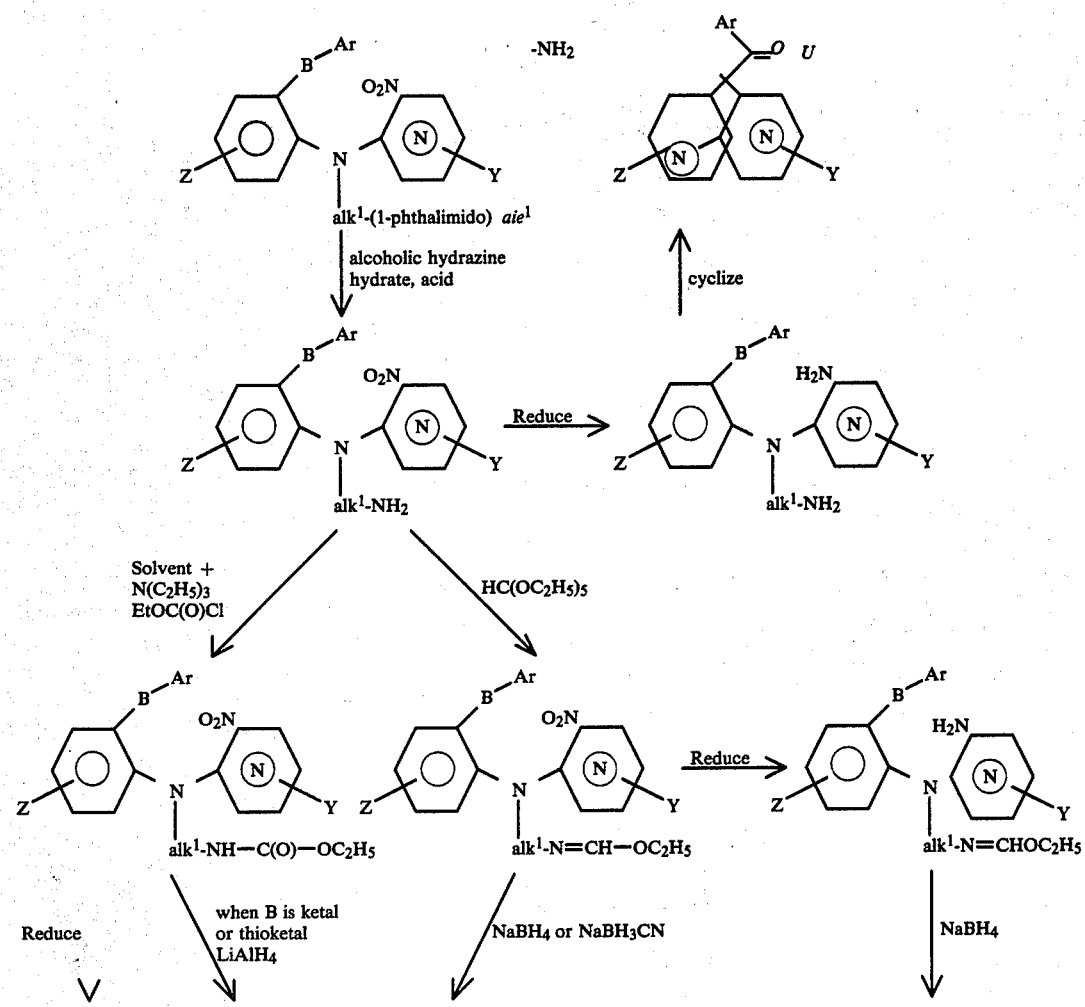

-continued
CHART II
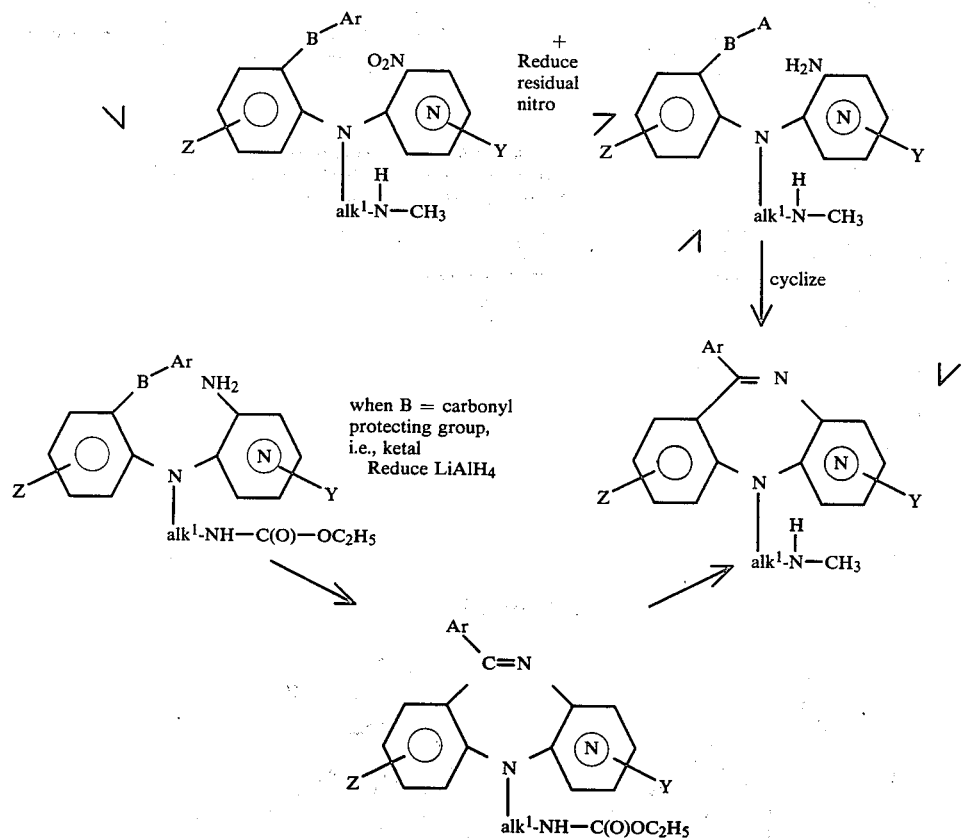
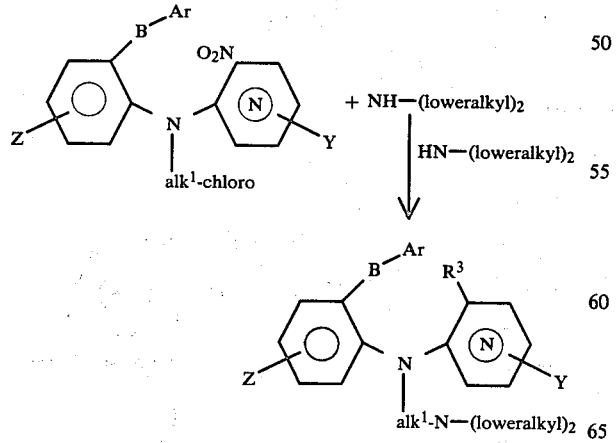
CHART III
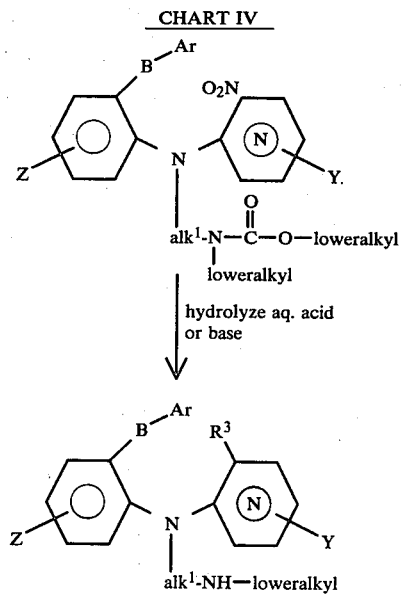
CHART IV

CHART V

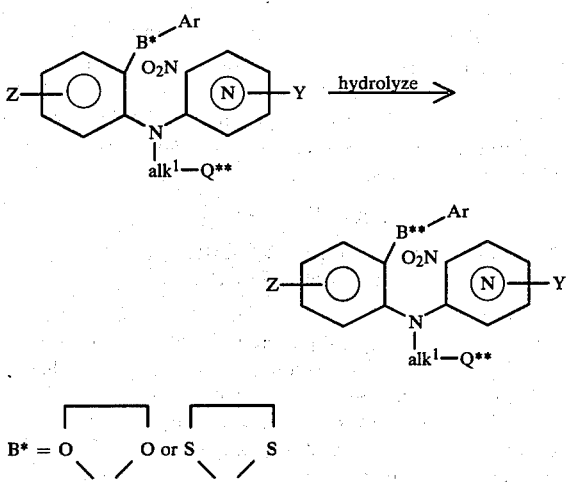

B* = O, O or S, S
       \ /    \ /
       —C—   —C—

B** is —C(O)— or —C(S)—

Q** is —NR$^1$R$^2$ whenever R$^1$ and R$^2$ are as defined above.

The preparation of the novel [2-[(nitropyridinyl)amino]phenyl]arylmethanones and the [2-[(aminopyridinyl)amino]phenyl]arylmethanones preparable therefrom are illustrated in the following examples and structurally in Table 1. Cyclization to the pyrido[1,4]benzodiazepines is also illustrated in the following examples and products thereof structurally in Table 2.

EXAMPLE 1

[2-[(3-Nitro-2-pyridinyl)amino]phenyl]phenylmethanone

A mixture of 56.0 g (0.28 mole) of 2-aminobenzophenone and 49.6 g (0.31 mole) of 2-chloro-3-nitropyridine was heated by means of an oil bath with stirring at 150° C. for 45 minutes (evolution of hydrogen chloride gas ceased). The product was partitioned between 130 ml of methylene chloride and 250 ml aqueous bicarbonate solution. The aqueous layer was extracted three times with 50 ml portions of methylene chloride. All methylene chloride solutions were combined and dried over sodium sulfate and filtered. Methylene chloride was stripped off in a rotary vacuum evaporator to give a dark brown viscous oil. The product was purified by column chromatography, eluting with methylene chloride on silica gel. On evaporation of the methylene chloride, an orange oil was obtained which crystallized slowly. The crystals were triturated in 105 ml of 1:1 tert-butyl alcohol/petroleum ether (30→60). Crystalline yellow solid, 50.5 g (58%) was obtained by centrifuging and drying, m.p. 85° C.

Analysis: Calculated for C$_{18}$H$_{13}$N$_3$O$_3$: % C,67.71; H,4.10; N,13.16. Found: C,67.34; H,4.07; N,13.12.

EXAMPLE 2

[2-[(3-Nitro-2-pyridinyl)amino]phenyl]phenylmethanone hydrochloride

A mixture of 56.0 g (0.28 mole) of 2-aminobenzophenone and 49.6 g (0.31 mole) of 2-chloro-3-nitropyridine was heated in an oil bath with stirring at 150° C. for 45 minutes. After cooling, an 8.7 g portion of the product was dissolved in 45 ml of methylene chloride, hydrogen chloride gas was added for 15 min and 100 ml of hexane was added. After stirring for 20 min, solid was collected and washed twice with 1:3 mixture of methylene chloride to hexanes. After drying in air, 8.2 g (81.6%) product was obtained.

EXAMPLE 3a

3-Chlorophenyl[2-[(3-nitro-2-pyridinyl)amino]phenyl]methanone

To a stirred melt of 10.0 g (0.043 mole) of 2-amino-3'-chlorobenzophenone under an atmosphere of nitrogen gas was added at 115°-120° C. in two portions at 20 min intervals, 6.3 g (0.040 mole) of 2-chloro-3-nitropyridine. The reaction mixture was heated at 125° C. for 4 hr and then poured into 250 ml of hot 3N hydrochloric acid under vigorous agitation. The mixture was cooled, the aqueous portion decanted and the residue was dissolved in 150 ml of methylene chloride. The methylene chloride solution was washed in sequence five times with 30 ml portions of 3N hydrochloric acid, once with 30 ml of 5% aqueous sodium hydroxide, once with 30 ml of saturated aqueous sodium chloride solution. The washed methylene chloride solution was dried over sodium sulfate and concentrated in vacuo. The residue was crystallized from isopropyl ether, yielding 4.23 g (28%) of dark yellow solid, m.p. 124°-125° C.

Analysis: Calculated for C$_{18}$H$_{12}$N$_3$O$_3$Cl: C,61.11; H,3.42; N,11.88. Found: C,60.88; H,3.40; N,11.75.

EXAMPLES 3b and c

When in the procedure of Example 3a equal molar amounts of the following are substituted for 2-amino-3'-chlorobenzophenone,
2-amino-5-methylbenzophenone, and
2-amino-4-methoxy-4'-chlorobenzophenone,
there are obtained:
3b  [2-[(3-nitro-2-pyridinyl)amino]-5-methylphenyl]-phenylmethanone, and
3c  4-chlorophenyl-[4-methoxy-2-[(3-nitro-2-pyridinyl)amino]phenyl]methanone.

EXAMPLES 4a to e

When in the procedure of Example 1, equal molar amounts of the following are substituted for 2-chloro-3-nitropyridine,
2-chloro-5-methoxy-3-nitropyridine,
3-chloro-4-nitropyridine,
5-chloro-2-methoxy-4-nitropyridine,
4-chloro-3-nitropyridine, and
3-chloro-2-nitropyridine
there are obtained:
a. [2-[(5-methoxy-3-nitro-2-pyridinyl)amino]phenyl]-phenylmethanone,
b. [2-[(4-nitro-3-pyridinyl)amino]phenyl]phenylmethanone,
c. [2-[(6-methoxy-4-nitro-3-pyridinyl)amino]phenyl]-phenylmethanone,
d. [2-[(3-nitro-4-pyridinyl)amino]phenyl]phenylmethanone, and
e. [2-[(2-nitro-3-pyridinyl)amino]phenyl]phenylmethanone.

EXAMPLES 5a to e

When in the procedure of Example 1 the following are substituted for 2-aminobenzophenone,
2-aminophenyl-2-thienylmethanone, 2-aminophenyl-3-thienylmethanone,
2-aminophenyl-2-pyridinylmethanone,
2-aminophenyl-3-pyridinylmethanone, and
2-aminophenyl-4-pyridinylmethanone,
there are obtained:
a. [2-[(3-nitro-2-pyridinyl)amino]phenyl]-2-thienylmethanone,
b. [2-[(3-nitro-2-pyridinyl)amino]phenyl]-3-thienylmethanone,
c. [2-[3-nitro-2-pyridinyl)amino]phenyl]-2-pyridinylmethanone,
d. [2-[3-nitro-2-pyridinyl)amino]phenyl]-3-pyridinylmethanone, and
e. [2-[3-nitro-2-pyridinyl)amino]phenyl]-4-pyridinylmethanone.

EXAMPLES 6a and b

When in the procedure of Example 1 equal molar amounts of the following are substituted for 2-aminobenzophenone,
2-amino-5-methylbenzophenone, and
2-amino-4'-chlorobenzophenone,
and equal molar amounts of 3-chloro-4-nitropyridine is substituted for 2-chloro-3-nitropyridine, there are obtained:
a. [5-methyl-2-[(4-nitro-3-pyridinyl)amino]phenyl]-phenylmethanone, and
b. (4-chlorophenyl)-[2-[(4-nitro-3-pyridinyl)amino]-phenyl]methanone.

EXAMPLES 7a to c

Following the procedure of Example 1 and substituting equal molar amounts of the following for 2-aminobenzophenone,
(2-aminophenyl)phenylmethanethione,
2-(2-phenyl-1,3-dioxolan-2-yl)benzeneamine, and
2-(2-phenyl-1,3-dithiolan-2-yl)benzeneamine,
there are obtained:
a. [2-[(3-nitro-2-pyridinyl)amino]phenyl]phenylmethanethione,
b. 3-nitro-N²-[2-(2-phenyl-1,3-dioxolan-2-yl)phenyl]-2-pyridineamine, and
c. 3-nitro-N²-[2-(2-phenyl-1,3-ditholan-2-yl)phenyl]-2-pyridineamine.

EXAMPLE 8a

[2-[[3-(Dimethylamino)propyl](3-nitro-2-pyridinyl)amino]phenyl]phenylmethanone

A mixture 2 g (0.006 mole) of [2-[(3-nitro-2-pyridinyl)amino]phenyl]phenylmethanone, 3 g (0.019 mole) of 3-dimethylaminopropyl chloride hydrochloride, 10 ml of 50% aqueous sodium hydroxide, 5 drops tricaprylylmethyl ammonium chloride (phase transfer catalyst) and 15 ml methylene chloride was stirred and maintained at reflux for 18 hrs. Chemical ionization mass spectral analysis indicated only a trace of the starting methanone was present with good conversion to the title compound. The reaction mixture was partially neutralized with 10% hydrochloric acid. The diluted but still basic mixture was extracted with methylene chloride and the methylene chloride layer evaporated to give 1.1 g brown residue predominantly the title compound.

EXAMPLE 8b

3-Chlorophenyl-[2-[[3-(dimethylamino)propyl](3-nitro-2-pyridinyl)amino]phenyl]methanone When in the procedure of Example 8a equal molar amounts of 3-chlorophenyl-[2-[(3-nitro-2-pyridinyl)amino]phenyl]methanone is substituted for [2-[(3-nitro-2-pyridinyl)amino]phenyl]phenylmethanone, the title compound is prepared.

EXAMPLE 8c

[2-[[3-(Dimethylamino)propyl](3-nitro-2-pyridinyl)amino]phenyl]phenylmethanone

A mixture of 3.6 g (0.01 mole) of [2-[(3-nitro-2-pyridinyl)amino]phenyl]phenylmethanone hydrochloride, 4.7 g (0.03 mole) of 3-dimethylaminopropyl chloride, 0.1 g of tricaprylyl ammonium chloride, 16 g (0.20 moles) of 50% aqueous sodium hydroxide, 25 ml methylene chloride, and 5 ml water was refluxed for 27 hrs. Chemical ionization mass spectroscopy analysis indicated the product was mainly the title compound. The mixture was cooled and diluted with methylenechloride-water mixture. The aqueous layer was extracted twice with methylene chloride. The combined methylene chloride layers were washed with aqueous sodium chloride solution, dried, treated with charcoal, filtered and evaporated to give 3.3 g black material (81.5%) which was predominantly the title compound as indicated by thin-layer chromatography and chemical ionization mass spectroscopy analysis of the chromatographed material, i.e. m/e=405.

EXAMPLES 9a to 9i

When in the procedure of Example 8a equal molar amounts of the following are substituted for [2-[(3-nitro-2-pyridinyl)amino]phenyl]phenylmethanone hydrochloride,
[2-[(3-nitro-2-pyridinyl)amino]-5-methylphenyl]phenylmethanone,
4-chlorophenyl[4-methoxy-2-[(3-nitro-2-pyridinyl)-]amino]phenylmethanone,
[2-[(5-methoxy-3-nitro-2-pyridinyl)amino]phenyl]-phenylmethanone,
[2-[(4-nitro-3-pyridinyl)amino]phenyl]phenylmethanone,
[5-methyl-2-[(4-nitro-3-pyridinyl)amino]phenyl]phenylmethanone,
(4-chlorophenyl)[2-[(4-nitro-3-pyridinyl)amino]-phenyl]methanone,
[2-[(6-methoxy-4-nitro-3-pyridinyl)amino]phenyl]-phenylmethanone,
[2-[(3-nitro-4-pyridinyl)amino]phenyl]phenylmethanone, and
[2-[(2-nitro-3-pyridinyl)amino]phenyl]phenylmethanone,
there are obtained:
a. [2-[[3-(dimethylamino)propyl](3-nitro-2-pyridinyl)amino]-5-methylphenyl]phenylmethanone,
b. [2-[[3-(dimethylamino)propyl](3-nitro-2-pyridinyl)amino]-4-methoxyphenyl](4-chlorophenyl)methanone.
c. [2-[[3-(dimethylamino)propyl](5-methoxy-3-nitro-2-pyridinyl)amino]phenyl]phenylmethanone,
d. [2-[[3-(dimethylamino)propyl](4-nitro-3-pyridinyl)amino]phenyl]phenylmethanone,
e. [2-[[3-(dimethylamino)propyl](4-nitro-3-pyridinyl)]amino]-5-methylphenyl]phenylmethanone, f. (4-chlorophenyl)[2-[[3-(dimethylamino)propyl](4-nitro-3-pyridinyl)amino]phenyl]methanone,
g. [2-[[3-dimethylamino)propyl](6-methoxy-4-nitro-3-pyridinyl)amino]phenyl]phenylmethanone,
h. [2-[[3-(dimethylamino)propyl](3-nitro-4-pyridinyl)amino]phenyl]phenylmethanone, and
i. [2-[[3-(dimethylamino)propyl](2-nitro-2-pyridinyl)amino]phenyl]phenylmethanone.

EXAMPLE 10

2-[3-[(2-Benzoylphenyl)(3-nitro-2-pyridinyl)amino]propyl]-1H-isoindole-1,3-(2H)dione Following the procedure of Example 8a and substituting N-(3-bromopropyl)phthalimide for 3-dimethylaminopropyl chloride hydrochloride, the title compound is obtained.

EXAMPLE 11

[3-[(2-Benzoylphenyl)(3-nitro-2-pyridinyl)]aminopropyl]methylcarbamic acid 1,1-dimethylethyl ester The title compound is prepared by reacting [2-[(3-nitro-2-pyridinyl)amino]phenyl]phenylmethanone and (3-chloropropyl)methylcarbamic acid tertiary-butyl ester.

EXAMPLE 12

[2-[(3-Chloropropyl)(3-nitro-2-pyridinyl)amino]phenyl]phenylmethanone

Following the procedure of Example 8a but substituting equal molar amounts of 1,3-dichloropropane for 3-dimethylaminopropyl chloride hydrochloride, the title compound is obtained.

EXAMPLE 13

[2-[[3-(Dimethylamino)propyl](3-nitro-2-pyridinyl)amino]phenyl]phenylmethanone

The title compound is prepared by reacting [2-[[3-chloropropyl](3-nitro-2-pyridinyl)amino]phenyl]methanone with dimethylamine.

EXAMPLES 14a and b

When in the procedure of Example 8a equal molar amounts of the following are substituted for 3-dimethylaminopropyl chloride hydrochloride,
2-dimethylaminoethyl chloride, and
4-dimethylaminobutyl chloride,
there are obtained,
a. [2-[[2-(dimethylamino)ethyl](3-nitro-2-pyridinyl)amino]phenyl]phenylmethanone, and
b. [2-[4-(dimethylamino)butyl](3-nitro-2-pyridinyl)amino]phenyl]phenylmethanone.

EXAMPLES 15a to d

When in the procedure of Example 8a the following are substituted for 3-dimethylaminopropyl chloride hydrochloride,
4-(3-chloropropyl)-morpholine hydrochloride,
N-(3-chloropropyl)-piperidine hydrochloride,
N-(3-chloropropyl)-pyrrolidine hydrochloride, and
N-(3-chloropropyl)-4-methyl-1-piperazinyl hydrochloride,
there are obtained:
a. [2-[[3-(4-morpholinyl)propyl](3-nitro-2-pyridinyl)amino]phenyl]phenylmethanone,
b. [2-[[3-(1-piperidinyl)propyl](3-nitro-2-pyridinyl)amino]phenyl]phenylmethanone,
c. [2-[3-(1-pyrrolidinyl)propyl](3-nitro-2-pyridinyl)amino]phenyl]phenylmethanone, and
d. [2-[[3-(4-methylpiperazin-1-yl-propyl)](3-nitro-2-pyridinyl)amino]phenyl]phenylmethanone.

EXAMPLES 16a to e

When in the procedure of Example 8a the following are substituted for [2-[(3-nitro-2-pyridinyl)amino]phenyl]phenylmethanone,
[2-[(3-nitro-2-pyridinyl)amino]phenyl]-2-thienylmethanone,
[2-[(3-nitro-2-pyridinyl)amino]phenyl]-3-thienylmethanone,
[2-[(3-nitro-2-pyridinyl)amino]phenyl]-2-pyridinylmethanone,
[2-[(3-nitro-2-pyridinyl)amino]phenyl]-3-pyridinylmethanone,
[2-[3-nitro-2-pyridinyl)amino]phenyl]-4-pyridinylmethanone,
there are obtained:
a. [2-[[3-(dimethylamino)propyl](3-nitro-2-pyridinyl)amino]phenyl]-2-thienylmethanone,
b. [2-[[3-(dimethylamino)propyl](3-nitro-2-pyridinyl)amino]phenyl]-3-thienylmethanone,
c. [2-[[3-(dimethylamino)propyl](3-nitro-2-pyridinyl)amino]phenyl]-2-pyridinylmethanone,
d. [2-[[3-(dimethylamino)propyl](3-nitro-2-pyridinyl)amino]phenyl]-2-pyridinylmethanone, and
e. [2-[[3-(dimethylamino)propyl](3-nitro-2-pyridinyl)amino]phenyl]-4-pyridinylmethanone.

EXAMPLE 17

[2-[(3-Aminopropyl)(3-nitro-2-pyridinyl)amino]phenyl]phenylmethanone

[2-[(3-Nitro-2-pyridinyl)amino]phenyl]phenylmethanone is reacted with (a) sodium hydride in solvent followed by N-(3-bromopropyl)phthalimide. The product of (a) is reacted with alcholic hydrazine hydrate and acid to give the title compound.

Alternately, the product of Example 10, 2-[3-[(2-benzoylphenyl)(3-nitro-2-pyridinyl)amino]propyl]-1H-isoindole-1,3-(2H)dione is reacted with alcoholic hydrazine hydrate and acid to give the title compound.

EXAMPLE 18

[2-[[3-(Methylamino)propyl](3-nitro-2-pyridinyl)amino]phenyl]phenylmethanone

[3-[(2-Benzoylphenyl)(3-nitro-2-pyridinyl)amino]propyl]methyl carbamic acid 1,1-dimethylethyl ester is hydrolyzed in an aqueous solution of hydrochloric acid to give the title compound.

EXAMPLES 19a and b

Following the procedure of Example 1 and substituting the following for 2-aminobenzophenone:
N-methyl-aminobenzophenone, and
N-ethyl-aminobenzophenone,
there are obtained:
[2-[N-methylamino-(3-nitro-2-pyridinyl)]phenyl]phenylmethanone, and
[2-[N-ethylamino-(3-nitro-2-pyridinyl)]phenyl]phenylmethanone.

EXAMPLE 20

[2-[(3-Amino-2-pyridinyl)amino]phenyl](3-chlorophenyl)methanone

A solution of 7.6 g (0.0215 mole) of 3-chlorophenyl[2-[(3-nitro-2-pyridinyl)amino]phenyl]methanone in 200 ml of ethyl acetate-ethanol (95:5) was shaken together with 1 g of Palladium hydroxide (20% on carbon) in a Parr bottle under 38.5 psi. hydrogen for 1.75 hr at room temperature. The mixture was filtered through celite. The filter cake was washed by suspending in methylene chloride three times and filtered. The methylene chloride extracts were combined with the ethyl acetate-ethanol filtrate and all concentrated in vacuo to give 4 g residue. The residue was dissolved in methyl alcohol and the solution acidified with 6N hydrochloric acid. After stirring 16 hr at room temperature, the mixture was basified with 10% sodium hydroxide and the methanol was removed in vacuo. Water, 50 ml, was added and the mixture extracted twice with methylene chloride. The combined methylene chloride extract was washed with water followed by washing with saturated sodium chloride solution, dried over sodium sulfate and concentrated in vacuo. The residue was twice recrystallized from isopropyl alcohol (charcoaled), yielding 1.09 g (15.7%) of brick red solid, m.p. 120°–121° C. (after a phase change at 108°–110° C.).

Analysis: Calculated for $C_{18}H_{14}N_3OCl$: C,66.77; H,4.36; N,12.98. Found: C,67.06; H,4.35; N,13.10.

EXAMPLE 21a

[2-[[3-(Dimethylamino)propyl](3-amino-2-pyridinyl)amino]phenyl]phenylmethanone A mixture of (0.05 mole) [2-[[3-(dimethylamino)propyl](3-nitro-2-pyridinyl)amino]phenyl]phenylmethanone, 13 g, (0.20 mole) of zinc dust, 2 g (0.05 mole) of sodium hydroxide in 75 ml ethanol and 25 ml water is stirred under reflux for 1 hr. The mixture is filtered and evaporated under reduced pressure. The residue is dissolved in methylene chloride and the resulting solution is dried over magnesium sulfate and decolorized with charcoal and filtered. The filtrate is evaporated to dryness to give the title compound in crude mixture.

EXAMPLE 21b

[2-[[3-(Dimethylamino)propyl](3-amino-2-pyridinyl)amino]phenyl]phenylmethanone Crude [2-[[3-(dimethylamino)propyl](3-nitro-2-pyridinyl)amino]phenyl]phenylmethanone, 1.1 g obtained in Example 8a was dissolved in methanol and hydrogenated in the presence of 5% palladium-on-carbon catalyst under 30 psi. hydrogen for 3 hr. The mixture was filtered and evaporated to a brown residue. $C^{13}$ nuclear magnetic resonance determination in

region showed signal for

and not

Chemical ionization mass spectroscopy showed the

was not due to starting material.

EXAMPLES 22a to 1

When in the procedure of Examples 21a, equal molar amounts of the following are substituted for [2-[[3-(dimethylamino)propyl](3-nitro-2-pyridinyl)amino]phenyl]phenylmethanone:

[2-[[3-(dimethylamino)propyl](3-nitro-2-pyridinyl)amino]-5-methylphenyl]phenylmethanone,

[2-[[3-(dimethylamino)propyl](3-nitro-2-pyridinyl)amino]-4-methoxyphenyl]-(4-chlorophenyl)methanone,

[2-[[3-(dimethylamino)propyl](5-methoxy-3-nitro-2-pyridinyl)amino]phenyl]phenylmethanone,

[2-[[3-(dimethylamino)propyl](4-nitro-3-pyridinyl)amino]phenyl]phenylmethanone,

[2-[[3-(dimethylamino)propyl](4-nitro-3-pyridinyl)amino]-5-methylphenyl]phenylmethanone, (4-chlorophenyl)[2-[[3-(dimethylamino)propyl](4-nitro-3-pyridinyl)amino]phenyl]methanone,

[2-[[3-(dimethylamino)propyl](6-methoxy-4-nitro-3-pyridinyl)amino]phenyl]phenylmethanone,

[2-[[3-(dimethylamino)propyl](3-nitro-4-pyridinyl)amino]phenyl]phenylmethanone,

[2-[[3-(dimethylamino)propyl](2-nitro-3-pyridinyl)amino]phenyl]phenylmethanone, 1,3-dihydro-2-[3-[(2-benzoylphenyl)(3-nitro-2-pyridinyl)amino]propyl]-1H-isoindole-1,3-dione,

[3-[(2-benzoylphenyl)(3-nitro-2-pyridinyl)]aminopropyl]methylcarbamic acid 1,1-dimethylethyl ester, and 3-chlorophenyl-[2-[[3-(dimethylamino)propyl](3-nitro-2-pyridinyl)amino]phenyl]methanone there are obtained:

a. [2-[(3-amino-2-pyridinyl)[3-(dimethylamino)propyl]amino]-5-methylphenyl]phenylmethanone, b. [2-[(3-amino-2-pyridinyl)[3-(dimethylamino)propyl]amino]-4-methoxyphenyl](4-chlorophenyl)methanone, c. [2-[(3-amino-5-methoxy-2-pyridinyl)[3-(dimethylamino)propyl]amino]phenyl]phenylmethanone, d. [2-[(4-amino-3-pyridinyl)]3-(dimethylamino)propyl]amino]phenyl]phenylmethanone, e. [2-[(4-amino-3-pyridinyl)[3-(dimethylamino)propyl]amino]-5-methylphenyl]phenylmethanone, f. [2-[(4-amino-3-pyridinyl)]3-(dimethylamino)propyl]aminophenyl]-4-chlorophenylmethanone, g. [2-[(4-amino-6-methoxy-3-pyridinyl)]3-(dimethylamino)propyl]amino]phenyl]phenylmethanone,
h. [2-[(3-amino-4-pyridinyl)[3-(dimethylamino)propyl]amino]phenyl]phenylmethanone,
i. [2-[(2-amino-3-pyridinyl)[3-(dimethylamino)propyl]amino]phenyl]phenylmethanone,
j. 2-[3-[(3-amino-2-pyridinyl)(2-benzoylphenyl)amino]propyl]-1H-isoindole-1,3-(2H)-dione,
k. [3-[(3-amino-2-pyridinyl)(2-benzoylphenyl)]aminopropyl]methylcarbamic acid 1,1-dimethylethyl ester, and
l. [3-[(3-amino-2-pyridinyl)[3-(dimethylamino)propyl]amino]phenyl]-3-chlorophenylmethanone.

EXAMPLES 23a and b

When in the procedure of Example 21a the following are substituted for [2-[[3-(dimethylamino)propyl](3-nitro-2-pyridinyl)amino]phenyl]phenylmethanone:
[2-[[2-(dimethylamino)ethyl](3-nitro-2-pyridinyl)amino]phenyl]phenylmethanone, and
[2-[[4-(dimethylamino)butyl](3-nitro-2-pyridinyl)amino]phenyl]phenylmethanone,
there are obtained:
a. [2-[[2-(dimethylamino)ethyl](3-amino-2-pyridinyl)amino]phenyl]phenylmethanone, and
b. [2-[[4-(dimethylamino)butyl](3-amino-2-pyridinyl)amino]phenyl]phenylmethanone.

EXAMPLES 24a to d

When in the procedure of Example 21a, the following are substituted for [2-[[3-(dimethylamino)propyl](3-nitro-2-pyridinyl)amino]phenyl]phenylmethanone:
[2-[[3-(4-morpholinyl)propyl](3-nitro-2-pyridinyl)amino]phenyl]phenylmethanone,
[2-[[3-(1-piperidinyl)propyl](3-nitro-2-pyridinyl)amino]phenyl]phenylmethanone,
[2-[[3-(1-pyrrolidinyl)propyl](3-nitro-2-pyridinyl)amino]phenyl]phenylmethanone, and
[2-[[3-(1-(4-methylpiperazin-1-yl)propyl)](3-nitro-2-pyridinyl)amino]phenyl]phenylmethanone,
there are obtained:
a. [2-[[3-(4-morpholinyl)propyl](3-amino-2-pyridinyl)amino]phenyl]phenylmethanone,
b. [2-[[3-(1-piperidinyl)propyl](3-amino-2-pyridinyl)amino]phenyl]phenylmethanone,
c. [2-[[3-(1-pyrrolidinyl)propyl](3-amino-2-pyridinyl)amino]phenyl]phenylmethanone, and
d. [2[[3-(4-methylpiperazin-1-yl)propyl)](3-amino-2-pyridinyl)amino]phenyl]phenylmethanone.

EXAMPLES 25a to e

When in the procedure of Example 21a the following are substituted for [2-[[3-(dimethylamino)propyl](3-nitro-2-pyridinyl)amino]phenyl]phenylmethanone:
[2-[[3-(dimethylamino)propyl](3-nitro-2-pyridinyl)amino]phenyl]-2-thienylmethanone,
[2-[[3-(dimethylamino)propyl](3-nitro-2-pyridinyl)amino]phenyl]-3-thienylmethanone,
[2-[[3-(dimethylamino)propyl](3-nitro-2-pyridinyl)amino]phenyl]-2-pyridinylmethanone,
[2-[[3-(dimethylamino)propyl](3-nitro-2-pyridinyl)amino]phenyl]-3-pyridinylmethanone, and
[2-[[3-(dimethylamino)propyl](3-nitro-2-pyridinyl)amino]phenyl]-4-pyridinylmethanone,
there are obtained:
a. [2-[(3-amino-2-pyridinyl)[3-(dimethylamino)propyl]amino]phenyl]-2-thienylmethanone,
b. [2-[(3-amino-2-pyridinyl)[3-(dimethylamino)propyl]amino]phenyl]-3-thienylmethanone,
c. [2-[(3-amino-2-pyridinyl)[3-(dimethylamino)propyl]amino]phenyl]-2-pyridinylmethanone,
d. [2-[(3-amino-2-pyridinyl)[3-(dimethylamino)propyl]amino]phenyl]-3-pyridinylmethanone, and
e. [2-[(3-amino-2-pyridinyl)[3-(dimethylamino)propyl]amino]phenyl]-4-pyridinylmethanone.

EXAMPLE 26

[2-[(3-Amino-2-pyridinyl)(3-aminopropyl)amino]phenyl]phenylmethanone

Following the procedure of Example 21a, [2-[(3-aminopropyl)(3-nitro-2-pyridinyl)amino]phenyl]phenylmethanone is reduced to give the title compound.

EXAMPLE 27

[2-[(3-Amino-2-pyridinyl)[3-(methylamino)propyl]amino]phenyl]phenylmethanone

Following the procedure of Example 21a, [2-[[3-(methylamino)propyl](3-nitro-2-pyridinyl)amino]phenyl]phenylmethanone is reduced to give the title compound.

EXAMPLE 28

N,N-Dimethyl-6-phenyl-11H-pyrido[2,3-b][1,4]benzodiazepine-11-propanamine

[2-[[3-(Dimethylamino)propyl](3-amino-2-pyridinyl)amino]phenyl]phenylmethanone from Example 21a is refluxed in excess acetic acid or in toluene solution containing a catalytic amount of p-toluene sulfonic acid to give a solution of the title compound.

EXAMPLE 29

N,N-Dimethyl-6-phenyl-11H-pyrido[2,3-b][1,4]benzodiazepine-11-propanamine fumarate [1:1]

Crude [2-[[3-(dimethylamino)propyl](3-nitro-2-pyridinyl)amino]phenyl]phenylmethanone is prepared as in Example 8c and dissolved in 75-25 volume mix of ethanol and water. Zinc dust and sodium hydroxide are added as in Example 21a and the mixture is refluxed until thin-layer chromatography shows reaction is complete. The mixture is filtered and the filtrate evaporated. The residue is added to acetic acid containing a small amount of p-toluene sulfonic acid and the solution refluxed until the reaction is complete. The solution is evaporated to dryness and the residue dissolved in hot isopropyl alcohol. The solution is decolorized with charcoal and filtered. Fumaric acid is added to the filtrate to give the title product as a precipitate. The melting point after recrystallization from isopropyl alcohol-isopropyl ether is 171°–173° C.

EXAMPLES 30a to d

When in the procedure of Example 28 the following are substituted for [2-[[3-(dimethylamino)propyl](3-amino-2-pyridinyl)amino]phenyl]phenylmethanone,
[2-[[3-(4-morpholinyl)propyl](3-amino-2-pyridinyl)amino]phenyl]methanone,
[2-[[3-(1-piperidinyl)propyl](3-amino-2-pyridinyl)amino]phenyl]phenylmethanone,
[2-[[3-(1-pyrrolidinyl)propyl](3-amino-2-pyridinyl)amino]phenyl]phenylmethanone, and
[2-[[3-(4-methylpiperazine-1-yl-propyl)](3-amino-2-pyridinyl)amino]phenyl]phenylmethanone, there are obtained:
a. 11-[[3-(4-morpholinyl)propyl]-6-phenyl-11H-pyrido[2,3-b][1,4]benzodiazepine,
b. 6-phenyl-11-[[3-(1-piperidinyl)propyl]-11H-pyrido[2,3-b][1,4]benzodiazepine,
c. 6-phenyl-11-[[3-(1-pyrrolidinyl)propyl]-11H-pyrido[2,3-b][1,4]benzodiazepine, and
d. 6-phenyl-11-[3-(4-methylpiperazin-1-yl)propyl]-11H-pyrido[2,3-b][1,4]benzodiazepine.

EXAMPLES 31a to e

When in the procedure of Example 28 the following are substituted for [2-[[3-(dimethylamino)propyl](3-amino-2-pyridinyl)amino]phenyl]phenylmethanone,
[2-[(3-amino-2-pyridinyl)[3-(dimethylamino)propyl]amino]phenyl]-2-thienylmethanone,
[2-[(3-amino-2-pyridinyl)[3-(dimethylamino)propyl]amino]phenyl]-3-thienylmethanone,
[2-[(3-amino-2-pyridinyl)[3-(dimethylamino)propyl]amino]phenyl]-2-pyridinylmethanone,
[2-[(3-amino-2-pyridinyl)[3-(dimethylamino)propyl]amino]phenyl]-3-pyridinylmethanone, and
[2-[(3-amino-2-pyridinyl)[3-(dimethylamino)propyl]amino]phenyl]-4-pyridinylmethanone,
there are obtained:
a. 11-[3-(dimethylamino)propyl]-6-(2-thienyl)-11H-pyrido[2,3-b][1,4]benzodiazepine,
b. 11-[3-(dimethylamino)propyl]-6-(3-thienyl)-11H-pyrido[2,3-b][1,4]benzodiazepine,
c. 11-[3-(dimethylamino)propyl]-6-(2-pyridinyl)-11H-pyrido[2,3-b][1,4]benzodiazepine,
d. 11-[3-(dimethylamino)propyl]-6-(3-pyridinyl)-11H-pyrido[2,3-b][1,4]benzodiazepine, and
e. 11-[3-(dimethylamino)propyl]-6-(4-pyridinyl)-11H-pyrido[2,3-b][1,4]benzodiazepine.

EXAMPLES 32a to l

When in the procedure of Example 28 the following are substituted for [2-[[3-(dimethylamino)propyl](3-amino-2-pyridinyl)amino]phenyl]phenylmethanone,
[2-[(3-amino-2-pyridinyl)[3-(dimethylamino)propyl]amino]-5-methylphenyl]phenylmethanone,
[2-[(3-amino-2-pyridinyl)[3-(dimethylamino)propyl]amino]-4-methoxyphenyl](4-chlorophenyl)methanone,
[2-[(3-amino-5-methoxy-2-pyridinyl)[3-(dimethylamino)propyl]amino]phenyl]phenylmethanone,
[2-[(4-amino-3-pyridinyl)[3-(dimethylamino)propyl]amino]phenyl]phenylmethanone,
[2-[(4-amino-3-pyridinyl)[3-(dimethylamino)propyl]amino]-5-methylphenyl]phenylmethanone,
[2-[(4-amino-3-pyridinyl)[3-(dimethylamino)propyl]amino]phenyl]-4-chlorophenylmethanone,
[2-[(4-amino-2-methoxy-5-pyridinyl)[3-(dimethylamino)propyl]amino]phenyl]phenylmethanone,
[2-[(3-amino-4-pyridinyl)[3-(dimethylamino)propyl]amino]phenyl]phenylmethanone,
[2-[(2-amino-3-pyridinyl)[3-(dimethylamino)propyl]amino]phenyl]phenylmethanone,
[2-3-[(3-amino-2-pyridinyl)(2-benzoylphenyl)amino]propyl]-1H-isoindole-1,3-(2H)-dione,
[2-[[2-(dimethylamino)ethyl](3-amino-2-pyridinyl)amino]phenyl]phenylmethanone, and
[2-[[4-(dimethylamino)butyl](3-amino-2-pyridinyl)amino]phenyl]phenylmethanone,
there are obtained:
a. N,N-dimethyl-8-methyl-6-phenyl-11H-pyrido[2,3-b][1,4]benzodiazepine-11-propanamine,
b. 6-(4-chlorophenyl)-N,N-dimethyl-9-methoxy-6-phenyl-11H-pyrido[2,3-b][1,4]benzodiazepine-11-propanamine,
c. N,N-dimethyl-3-methoxy-6-phenyl-11H-pyrido[2,3-b][1,4]benzodiazepine-11-propanamine,
d. N,N-dimethyl-6-phenyl-11H-pyrido[3,4-b][1,4]benzodiazepine-11-propanamine,
e. N,N-dimethyl-8-methyl-6-phenyl-11H-pyrido[3,4-b][1,4]benzodiazepine-11-propanamine,
f. 6-(4-chlorophenyl)-N,N-dimethyl-11H-pyrido[3,4-b][1,4]benzodiazepine-11-propanamine,
g. N,N-dimethyl-3-methoxy-6-phenyl-11H-pyrido[3,4-b][1,4]benzodiazepine-11-propanamine,
h. N,N-dimethyl-10-phenyl-5H-pyrido[4,3-b][1,4]benzodiazepine-5-propanamine,
i. N,N-dimethyl-10-phenyl-5H-pyrido[3,2-b][1,4]benzodiazepine-5-propanamine,
j. 11-[3-(1,3-dihydro-1,3-dioxo-2H-isoindol-2-yl)propyl]-6-phenyl-11H-pyrido[2,3-b][1,4]benzodiazepine,
k. N,N-dimethyl-6-phenyl-11H-pyrido[2,3-b][1,4]benzodiazepine-11-ethanamine, and
l. N,N-dimethyl-6-phenyl-11H-pyrido[2,3-b][1,4]benzodiazepine-11-butanamine,

EXAMPLE 33

N,N-Dimethyl-6-phenyl-11H-pyrido[2,3-b][1,4]benzodiazepine-11-propanamine

To a stirred solution of 3.3 g of crude [2-[[3-(dimethylamino)propyl](3-nitro-2-pyridinyl)amino]phenyl]phenylmethanone obtained in Example 8(c) in 20 ml of acetic acid at 65° C. was added portionwise 6.6 g of iron powder. The reaction was exothermic at the beginning, the temperature rising to 90° C. Thereafter the temperature was controlled at 85° C. for 1 hr. The mixture was filtered through celite and washed with acetic acid and methanol. The filtrate and washes were combined and evaporated and the residue was dissolved in methanol. The solution was filtered to remove insoluble iron acetate. The filtrate was evaporated and the residue dissolved in water/methylene chloride and made basic with sodium hydroxide and potassium carbonate. The mixture was mixed with celite and filtered through celite. The aqueous layer of the filtrate was extracted twice with methylene chloride which had been used to wash the cake. The combined methylene chloride solution was washed once with NaCl solution, dried and treated with charcoal, filtered and evaporated to give a black foam weighing 1.63 g (46%). The foam was dissolved in isopropyl alcohol. The solution was treated with charcoal and the mixture was filtered into a solution of 0.7 g fumaric acid in isopropyl alcohol. This solution was again treated with charcoal and filtered. Chemical ionization mass spectral analysis and thin-layer chromatography confirmed the presence of the title compound.

EXAMPLE 34

(2-Chlorophenyl)[2-[(3-nitro-2-pyridinyl)amino]phenyl]methanone

Under nitrogen atmosphere, 44.4 g (0.192 mole) of 2-amino-2'-chlorobenzophenone was added in four portions at 15 min intervals to a stirred melt (130°–135° C.) of 33.5 g (0.211 mole) of 2-chloro-3-nitropyridine. Heating was continued for 30 min at 130°–135° C. and for 45 min at 145° C. The reaction mixture was cooled to 110° C. and 200 ml of hot toluene was added. To the cooled mixture (room temperature) 100 ml of 10% aqueous sodium hydroxide was added and stirring was continued for 15 min. The toluene layer was separated and washed three times with 75 ml portions of water, dried over sodium sulfate and concentrated in vacuo. The residue was dissolved in 300 ml of methylene chloride and the solution was stirred with 100 g of fluorisil for 30 min. The mixture was filtered, rinsing with fluorisil filter-cake several times with methylene chloride. The combined filtrates were treated in the same manner with an additional 100 g of fluorisil. The methylene chloride was separated by filtration and concentrated in vacuo. The residue was crystallized from ethyl acetate-cyclohexane to give 26.0 g of a bright yellow solid, m.p. 119° C. A second crop (7.0 g) was obtained from the filtrate and recrystallized from isopropyl ether, m.p. 118°–119° C. The total yield amounted to 49% of theory.

Analysis: Calculated for $C_{18}H_{12}N_3O_3Cl$: C, 61.11; H,3.42; N,11.88. Found: C,61.47; H,3.43; N,11.79.

EXAMPLE 35

(4-Chlorophenyl)[2-[(3-nitro-2-pyridinyl)amino]phenyl]methanone

Under nitrogen atmosphere, 50.0 g (0.216 mole) of 2-amino-4'-chlorobenzophenone was added in four portions at 15 min intervals to a stirred melt (105°–110° C.) of 35.9 g (0.227 mole) of 2-chloro-3-nitropyridine. The reaction temperature was increased to 120° C. for 3 hr and then to 150° C. for 2 hr. The stirred mixture was cooled to 115° C. and 100 ml of hot toluene was added. The cooled mixture (room temperature) was filtered. The filtrate was washed with 75 ml of 5% sodium hydroxide solution, 50 ml of water and 30 ml of saturated sodium chloride solution, dried over sodium sulfate and concentrated in vacuo. The residue was crystallized from ethyl acetate-isopropyl ether to give 43 g (56.4%) solid. Recrystallization from ethyl acetate-isopropyl ether gave 18.26 g* of bright-yellow solid, m.p. 138'–140° C.

Analysis: Calculated for $C_{18}H_{12}N_3O_3Cl$: C,61.11; H,3.42; N,11.88. Found: C,61.09; H,3.37; N,11.81.
*An additional 9.6 g of material was obtained from the filtrate.

EXAMPLE 36

(3-Fluorophenyl)[2-[(3-nitro-2-pyridinyl)amino]phenyl]methanone

Under nitrogen atmosphere, 45.0 g (0.209 mole) of 2-amino-3'-fluorobenzophenone was added in four portions at 15 min intervals to a stirred melt (120°–125° C.) of 38.2 g (0.241 mole) of 2-chloro-3-nitropyridine. The reaction mixture was heated at 120°–125° C. for one hr. and then at 145°–150° C. for 45 min. The mixture was cooled to 130° C. and 100 ml of toluene was added. The cooled mixture (room temperature) was diluted with 100 ml of ethyl acetate and extracted with 100 ml of 10% potassium hydroxide. The organic layer was extracted with three 100 ml portions of 3N hydrochloric acid, 100 ml of water and 50 ml of saturated sodium chloride solution, dried over sodium sulfate and concentrated in vacuo. The residue was crystallized from ethyl acetate-isopropyl ether to give 35.5 g (50%) solid. The solid was dissolved in 200 ml of methylene chloride and the solution stirred with 50 g of fluorisil for 2 hr. The mixture was filtered and the filtrate was concentrated in vacuo. A 5 g portion of the residue was recrystallized from ethyl acetate-isopropyl ether to give 4.1 g of yellow-orange solid, m.p. 98°–101° C.

Analysis: Calculated for $C_{18}H_{12}N_3O_3F$: C,64.10; H,3.58; N,12.46. Found: C,64.13; H,3.52; N,12.43.

EXAMPLE 37

3-(Fluorophenyl)[2-[methyl(3-nitro-2-pyridinyl)amino]phenyl]methanone

Under nitrogen atmosphere, a solution of 3.4 g (0.010 mole) of (3-fluorophenyl)[2-[(3-nitro-2-pyridinyl)amino]phenyl]methanone in 20 ml of dry dimethylformamide was added dropwise to a stirred suspension of 0.6 g (0.013 mole) of sodium hydride (50% in oil) in 20 ml of dimethylformamide. The reaction mixture was stirred at room temperature for 30 min, then at 55°–60° C. for 3 hr. The mixture was chilled to 10° C. and 2.9 g (0.020 mole) of methyl iodide was added. The mixture was stirred at room temperature for 16 hr in a stoppered flask and then poured into 200 ml of ice water. The mixture was basified to pH 14 with 10% sodium hydroxide solution and extracted three times with 50 ml portions of ethyl acetate. The combined ethyl acetate extracts were washed with four 75 ml portions of water, 25 ml of saturated sodium chloride, dried over sodium sulfate and concentrated in vacuo. The residue was dissolved in ether and the solution stirred with 15 g of fluorisil for one hr. The mixture was filtered, rising the fluorisil several times with ether. The combined filtrates were concentrated in vacuo and the residue twice recrystallized from isopropyl ether-ethyl acetate to give 1.5 g (43%) of a dark-gold solid, m.p. 117°–119° C.

Analysis: Calculated for $C_{19}H_{16}N_3O_3F$: C,64.95; H,4.02; N,11.06. Found: C,64.98; H,3.96; N,11.84.

EXAMPLE 38

When in the procedure of Example 8a, equal molar amounts of the following are substituted for 3-chlorophenyl-[2-[(3-nitro-2-pyridinyl)amino]phenyl]methanone:

(2-chlorophenyl)[2-[(3-nitro-2-pyridinyl)amino]phenyl]methanone,
(4-chlorophenyl)[2-[(3-nitro-2-pyridinyl)amino]phenyl]methanone, and
(3-fluorophenyl)[2-[(3-nitro-2-pyridinyl)amino]phenyl]methanone,
there are obtained:
a. 2-chlorophenyl-[2-[3-(dimethylamino)propyl](3-nitro-2-pyridinyl)amino]phenylmethanone,
b. 4-chlorophenyl-[2-[3-(dimethylamino)propyl](3-nitro-2-pyridinyl)amino]phenylmethanone, and
c. 3-fluorophenyl[2-(3-nitro-2-pyridinyl)amino]phenylmethanone.

EXAMPLE 39

[2-[(3-Amino-2-pyridinyl)amino]phenyl](4-chlorophenyl)methanone

Under an atmosphere of nitrogen, 29 g (0.187 mole) of titanium trichloride was added portionwise (cautiously; in hood) to 200 g of ice and the resulting solution was diluted to 250 ml volume with water. This was added, all at once, at 30° C. to a stirred solution of 11.0 g (0.0312 mole) of (4-chlorophenyl)[2-[(3-nitro-2-pyridinyl)amino]phenyl]methanone, 300 ml of ethyl acetate: methanol (1:1), 100 ml of acetic acid: water (1:1) and 20 ml more solution of titanium trichloride. The reaction mixture was stirred for 20 min then diluted with one liter of water and filtered. The filter cake was washed with water and then partitioned between 200 ml of methylene chloride and 75 ml of 10% aqueous sodium hydroxide solution. The methylene chloride layer was washed with 75 ml of water, dried over sodium sulfate and concentrated in vacuo. The residue (7 g) was recrystallized from ethyl acetate-isopropyl ether to give 6.0 g of gold solid, m.p. 145°–146° C.

Analysis: Calculated for $C_{18}H_{14}N_3OCl$: C,66.77; H,4.36; N,12.98. Found: C,66.63; H,4.32; N,12.98.

EXAMPLE 40

[2-[(3-Amino-2-pyridinyl)amino]phenyl](3-fluorophenyl)methanone

Under an atmosphere of nitrogen, 30 g of titanium trichloride was added portionwise (cautiously) with stirring to 200 ml of ice. The resulting solution was added all at once to a stirred solution of 10.0 g (0.0297 mole) of (3-fluorophenyl)[2-[(3-nitro-2-pyridinyl)amino]phenyl]methanone in 150 ml of acetic acid: ethanol (1:1) and 150 ml of acetic acid: water (1:1). After 30 min stirring, the reaction mixture was poured into one liter of water. The mixture was filtered and the resulting filter-cake was suspended in 100 ml of water. The mixture was again filtered and the filter-cake (10.0 g) was partially dissolved in 100 ml of hot methanol. The solution was basified with 25 ml of concentrated ammonium hydroxide, stirred for an additional 15 min and then diluted with 500 ml of water. The mixture was extracted three times with 75 ml portions of methylene chloride. The combined methylene chloride extracts were washed with 50 ml of water, dried over sodium sulfate and concentrated in vacuo. The residue (6.9 g) was twice recrystallized, treating once with charcoal, from ethyl acetate-isopropyl ether to give 4.5 g (49%) of a dark gold solid, m.p. 135°–137° C.

Analysis: Calculated for $C_{18}H_{14}N_3OF$: C,70.35; H,4.59; N,13.67. Found: C,70.29; H,4.56; N,13.68.

EXAMPLE 41

[2-[(3-Amino-2-pyridinyl)amino]phenyl](2-chlorophenyl)methanone

Following the procedure of Example 39, (2-chlorophenyl)[2-[(3-nitro-2-pyridinyl)amino]phenyl]methanone is reduced to give the title compound.

EXAMPLE 42

6-(3-Chlorophenyl)-N,N-dimethyl-11H-pyrido[2,3-b][1,4]benzodiazepine-11-propanamine

[3-[(3-Amino-2-pyridinyl)3-(dimethylamino)propyl]amino]phenyl-3-chlorophenylmethanone is refluxed in excess acetic acid or in toluene solution containing a catalytic amount of p-toluene sulfonic acid to give the title compound.

TABLE 1

| Ex. No. | B | R | Ar | Y | Z | Salt |
|---|---|---|---|---|---|---|
| 1 | —C(O)— | H | $C_6H_5$— | H | H | — |
| 2 | —C(O)— | H | $C_6H_5$— | H | H | HCl |
| 3 (a) | —C(O)— | H | 3-Cl—$C_6H_4$— | H | H | — |
| 3 (b) | —C(O)— | H | $C_6H_5$— | H | 5-$CH_3$ | — |
| 3 (c) | —C(O)— | H | 4-Cl—$C_6H_4$— | H | 4-$OCH_3$ | — |
| 4 (a) | —C(O)— | H | $C_6H_5$— | 5-$OCH_3$ | H | — |
| 5 (a) | —C(O)— | H | 2-thienyl | H | H | — |
| 5 (b) | —C(O)— | H | 3-thienyl | H | H | — |
| 5 (c) | —C(O)— | H | 2-pyridinyl | H | H | — |
| 5 (d) | —C(O)— | H | 3-pyridinyl | H | H | — |
| 5 (e) | —C(O)— | H | 4-pyridinyl | H | H | — |
| 7 (a) | —C(S)— | H | $C_6H_5$— | H | H | — |
| 7 (b) | —C(O,O)— (ketal) | H | $C_6H_5$— | H | H | — |
| 7 (c) | —C(S,S)— (dithioketal) | H | $C_6H_5$— | H | H | — |
| 8 (a) | —C(O)— | —$(CH_2)_3N(CH_3)_2$ | $C_6H_5$— | H | H | — |
| 8 (b) | —C(O)— | —$(CH_2)_3N(CH_3)_2$ | 3-Cl—$C_6H_4$— | H | H | — |
| (c) | —C(O)— | —$(CH_2)_3N(CH_3)_2$ | $C_6H_5$— | H | H | — |
| 9 a | —C(O)— | —$(CH_2)_3N(CH_3)_2$ | $C_6H_5$— | H | 5-$CH_3$ | — |
| 9 b | —C(O)— | —$(CH_2)_3N(CH_3)_2$ | 4-Cl—$C_6H_4$— | H | 4-$OCH_3$ | — |
| 9 c | —C(O)— | —$(CH_2)_3N(CH_3)_2$ | $C_6H_5$— | 5-$OCH_3$ | H | — |
| 10 | —C(O)— | —$(CH_2)_3$—1-phthalimido | $C_6H_5$— | H | H | — |
| 11 | —C(O)— | —$(CH_2)_3N(CH_3)$[C(O)O—C(CH_3)_3$] | $C_6H_5$— | H | H | — |
| 12 | —C(O)— | —$(CH_2)_3Cl$ | $C_6H_5$— | H | H | — |

TABLE 1-continued

| Ex. No. | B | R | Ar | Y | Z | Salt |
|---|---|---|---|---|---|---|
| 13 | —C(O)— | —(CH$_2$)$_3$N(CH$_3$)$_2$ | C$_6$H$_5$— | H | H | — |
| 14 a | —C(O)— | —(CH$_2$)$_2$N(CH$_3$)$_2$ | C$_6$H$_5$— | H | H | — |
| 14 b | —C(O)— | —(CH$_2$)$_4$N(CH$_3$)$_2$ | C$_6$H$_5$— | H | H | — |
| 15 a | —C(O)— | —(CH$_2$)$_3$(4-morpholinyl) | C$_6$H$_5$— | H | H | — |
| 15 b | —C(O)— | —(CH$_2$)$_3$—1-piperidinyl | C$_6$H$_5$— | H | H | — |
| 15 c | —C(O)— | —(CH$_2$)$_3$—1-pyrrolidinyl | C$_6$H$_5$— | H | H | — |
| 15 d | —C(O)— | —(CH$_2$)$_3$—(4-methyl)-1-piperazine | C$_6$H$_5$— | H | H | — |
| 16 a | —C(O)— | —(CH$_2$)$_3$N(CH$_3$)$_2$ | 2-thienyl | H | H | — |
| 16 b | —C(O)— | —(CH$_2$)$_3$N(CH$_3$)$_2$ | 3-thienyl | H | H | — |
| 16 c | —C(O)— | —(CH$_2$)$_3$N(CH$_3$)$_2$ | 2-pyridinyl | H | H | — |
| 16 d | —C(O)— | —(CH$_2$)$_3$N(CH$_3$)$_2$ | 3-pyridinyl | H | H | — |
| 16 e | —C(O)— | —(CH$_2$)$_3$N(CH$_3$)$_2$ | 4-pyridinyl | H | H | — |
| 17 | —C(O)— | —(CH$_2$)$_3$NH$_2$ | C$_6$H$_5$— | H | H | — |
| 18 | —C(O)— | —(CH$_2$)$_3$NHCH$_3$ | C$_6$H$_5$— | H | H | — |
| 19 a | —C(O)— | —CH$_3$ | C$_6$H$_5$— | H | H | — |
| 19 b | —C(O)— | —C$_2$H$_5$ | C$_6$H$_5$— | H | H | — |
| 34 | —C(O)— | H | 2-Cl—C$_6$H$_4$— | H | H | — |
| 35 | —C(O)— | H | 4-Cl—C$_6$H$_4$— | H | H | — |
| 36 | —C(O)— | H | 3-F—C$_6$H$_4$— | H | H | — |
| 37 | —C(O)— | —CH$_3$ | 3-F—C$_6$H$_4$— | H | H | — |
| 38 a | —C(O)— | —(CH$_2$)$_3$N(CH$_3$)$_2$ | 2-Cl—C$_6$H$_4$— | H | H | — |
| b | —C(O)— | —(CH$_2$)$_3$N(CH$_3$)$_2$ | 4-Cl—C$_6$H$_4$— | H | H | — |
| c | —C(O)— | —(CH$_2$)$_3$N(CH$_3$)$_2$ | 3-F—C$_6$H$_4$— | H | H | — |

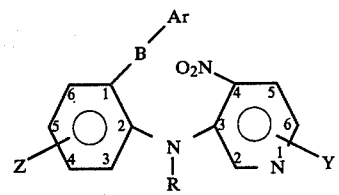

| | | | | | | |
|---|---|---|---|---|---|---|
| 4 b | —C(O)— | H | C$_6$H$_5$— | H | H | — |
| 4 c | —C(O)— | H | C$_6$H$_5$— | 6-OCH$_3$ | H | — |
| 6 a | —C(O)— | H | C$_6$H$_5$— | H | 5-CH$_3$ | — |
| 6 b | —C(O)— | H | 4 Cl—C$_6$H$_4$— | H | H | — |
| 9 d | —C(O)— | —(CH$_2$)$_3$N(CH$_3$)$_2$ | C$_6$H$_5$— | H | H | — |
| 9 e | —C(O)— | —(CH$_2$)$_3$N(CH$_3$)$_2$ | C$_6$H$_5$— | H | 5-CH$_3$ | — |
| 9 f | —C(O)— | —(CH$_2$)$_3$N(CH$_3$)$_2$ | 4-Cl—C$_6$H$_4$— | H | H | — |
| 9 g | —C(O)— | —(CH$_2$)$_3$N(CH$_3$)$_2$ | C$_6$H$_5$— | 6-OCH$_3$ | H | — |

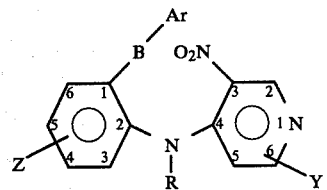

| | | | | | | |
|---|---|---|---|---|---|---|
| 4 d | —C(O)— | H | C$_6$H$_5$— | H | H | — |
| 9 h | —C(O)— | —(CH$_2$)$_3$N(CH$_3$)$_2$ | C$_6$H$_5$— | H | H | — |

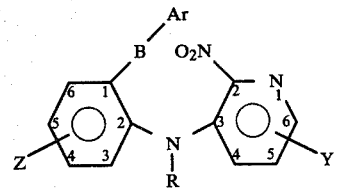

| | | | | | | |
|---|---|---|---|---|---|---|
| 4 e | —C(O)— | H | 4-Cl—C$_6$H$_4$— | H | H | — |
| 9 i | —C(O)— | —(CH$_2$)$_3$N(CH$_3$)$_2$ | C$_6$H$_5$— | H | H | — |

TABLE 2

| Ex. No. | B | R | Ar | Y | Z | Salt |
|---|---|---|---|---|---|---|

Structure 1:
$$\text{Z}-\underset{\underset{4\;3}{5\;2\;1}}{\text{ring}}-\underset{R}{N}-\underset{\underset{3\;4}{2\;1\;6}}{\text{ring}}-Y, \text{ with } B-Ar \text{ at position 1 and } H_2N \text{ at position 3}$$

| Ex. No. | B | R | Ar | Y | Z | Salt |
|---|---|---|---|---|---|---|
| 20 | —C(O)— | H | 3-Cl—C$_6$H$_4$— | H | H | — |
| 21 a | —C(O)— | —(CH$_2$)$_3$N(CH$_3$)$_2$ | C$_6$H$_5$— | H | H | — |
| 21 b | —C(O)— | —(CH$_2$)$_3$N(CH$_3$)$_2$ | C$_6$H$_5$— | H | H | — |
| 22 a | —C(O)— | —(CH$_2$)$_3$N(CH$_3$)$_2$ | C$_6$H$_5$— | H | 5-CH$_3$ | — |
| 22 b | —C(O)— | —(CH$_2$)$_3$N(CH$_3$)$_2$ | 4-Cl—C$_6$H$_4$— | H | 4-OCH$_3$ | — |
| 22 c | —C(O)— | —(CH$_2$)$_3$N(CH$_3$)$_2$ | C$_6$H$_5$— | 5-OCH$_3$ | H | — |
| 22 j | —C(O)— | —(CH$_2$)$_3$—1-phthamimido | C$_6$H$_5$— | H | H | — |
| 22 k | —C(O)— | —(CH$_2$)$_3$N(CH$_3$)[C(O)OC(CH$_3$)$_3$] | C$_6$H$_5$— | H | H | — |
| 22 l | —C(O)— | —(CH$_2$)$_3$N(CH$_3$)$_2$ | 3-Cl—C$_6$H$_4$— | H | H | — |
| 23 a | —C(O)— | —(CH$_2$)$_2$N(CH$_3$)$_2$ | C$_6$H$_5$— | H | H | — |
| 23 b | —C(O)— | —(CH$_2$)$_4$N(CH$_3$)$_2$ | C$_6$H$_5$— | H | H | — |
| 24 a | —C(O)— | —(CH$_2$)$_3$—4-morpholinyl | C$_6$H$_5$— | H | H | — |
| 24 b | —C(O)— | —(CH$_2$)$_3$—1-piperidinyl | C$_6$H$_5$— | H | H | — |
| 24 c | —C(O)— | —(CH$_2$)$_3$—1-pyrrolidinyl | C$_6$H$_5$— | H | H | — |
| 24 d | —C(O)— | —(CH$_2$)$_3$—(4-methyl-1-piperazinyl | C$_6$H$_5$— | H | H | — |
| 25 a | —C(O)— | —(CH$_2$)$_3$N(CH$_3$)$_2$ | 2-thienyl | H | H | — |
| 25 b | —C(O)— | —(CH$_2$)$_3$N(CH$_3$)$_2$ | 3-thienyl | H | H | — |
| 25 c | —C(O)— | —(CH$_2$)$_3$N(CH$_3$)$_2$ | 2-pyridinyl | H | H | — |
| 25 d | —C(O)— | —(CH$_2$)$_3$N(CH$_3$)$_2$ | 3-pyridinyl | H | H | — |
| 25 e | —C(O)— | —(CH$_2$)$_3$N(CH$_3$)$_2$ | 4-pyridinyl | H | H | — |
| 26 | —C(O)— | —(CH$_2$)$_3$NH$_2$ | C$_6$H$_5$— | H | H | — |
| 27 | —C(O)— | —(CH$_2$)$_3$NHCH$_3$ | C$_6$H$_5$— | H | H | — |
| 39 | —C(O)— | H | 4-Cl—C$_6$H$_4$— | H | H | — |
| 40 | —C(O)— | H | 3-F—C$_6$H$_4$— | H | H | — |
| 41 | —C(O)— | H | 2-Cl—C$_6$H$_4$— | H | H | — |

Structure 2 (pyridine at right ring, N at position 1; H$_2$N at position 4):

| Ex. No. | B | R | Ar | Y | Z | Salt |
|---|---|---|---|---|---|---|
| 22 d | —C(O)— | —(CH$_2$)$_3$N(CH$_3$)$_2$ | C$_6$H$_5$— | H | H | — |
| 22 e | —C(O)— | —(CH$_2$)$_3$N(CH$_3$)$_2$ | C$_6$H$_5$— | H | 5-CH$_3$ | — |
| 22 f | —C(O)— | —(CH$_2$)$_3$N(CH$_3$)$_2$ | 4-Cl—C$_6$H$_4$— | H | H | — |
| 22 g | —C(O)— | —(CH$_2$)$_3$N(CH$_3$)$_2$ | C$_6$H$_5$— | -2-OCH$_3$ | H | — |

Structure 3 (pyridine N at position 1, H$_2$N at 3, ring fused differently):

| Ex. No. | B | R | Ar | Y | Z | Salt |
|---|---|---|---|---|---|---|
| 4 d | —C(O)— | H | C$_6$H$_5$— | H | H | — |
| 9 h | —C(O)— | —(CH$_2$)$_3$N(CH$_3$)$_2$ | C$_6$H$_5$— | H | H | — |
| 22 h | —C(O)— | —(CH$_2$)$_3$N(CH$_3$)$_2$ | C$_6$H$_5$— | H | H | — |

Structure 4 (pyrimidine/pyridazine variant):

| Ex. No. | B | R | Ar | Y | Z | Salt |
|---|---|---|---|---|---|---|
| 4 e | —C(O)— | H | 4-Cl—C$_6$H$_4$— | H | H | — |
| 9 i | —C(O)— | —(CH$_2$)$_3$N(CH$_3$)$_2$ | C$_6$H$_5$— | H | H | — |

TABLE 2-continued

| Ex. No. | B | R | Ar | Y | Z | Salt |
|---|---|---|---|---|---|---|
| 22 i | —C(O)— | —(CH$_2$)$_3$N(CH$_3$)$_2$ | C$_6$H$_5$— | H | H | — |

TABLE 3

| Ex. No. | R | Ar | Y | Z | Salt |
|---|---|---|---|---|---|

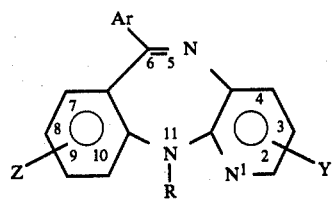

| | | | | | |
|---|---|---|---|---|---|
| 28 | —(CH$_2$)$_3$N(CH$_3$)$_2$ | C$_6$H$_5$— | H | H | — |
| 29 | —(CH$_2$)$_3$N(CH$_3$)$_2$ | C$_6$H$_5$— | H | H | fumarate |
| 30 (a) | —(CH$_2$)$_3$—(4-morpholinyl) | C$_6$H$_5$— | H | H | — |
| 30 (b) | —(CH$_2$)$_3$—(1-piperidinyl) | C$_6$H$_5$— | H | H | — |
| 30 (c) | —(CH$_2$)$_3$—(1-pyrrolidinyl) | C$_6$H$_5$— | H | H | — |
| 30 (d) | —(CH$_2$)$_3$—(4-methyl-piperazin-1-yl) | C$_6$H$_5$ | H | H | — |
| 31 (a) | —(CH$_2$)$_3$N(CH$_3$)$_2$ | 2-thienyl | H | H | — |
| 31 (b) | —(CH$_2$)$_3$N(CH$_3$)$_2$ | 3-thienyl | H | H | — |
| 31 (c) | —(CH$_2$)$_3$N(CH$_3$)$_2$ | 2-pyridinyl | H | H | — |
| 31 (d) | —(CH$_2$)$_3$N(CH$_3$)$_2$ | 3-pyridinyl | H | H | — |
| 31 (e) | —(CH$_2$)$_3$N(CH$_3$)$_2$ | 5-pyridinyl | H | H | — |
| 32 (a) | —(CH$_2$)$_3$N(CH$_3$)$_2$ | C$_6$H$_5$— | H | 8-CH$_3$ | — |
| 32 (b) | —(CH$_2$)$_3$N(CH$_3$)$_2$ | 4-Cl—C$_6$H$_4$— | H | 9-OCH$_3$ | — |
| 32 (c) | —(CH$_2$)$_3$N(CH$_3$)$_2$ | C$_6$H$_5$— | 3-OCH$_3$ | H | — |
| 32 (j) | —(CH$_2$)$_3$(1-phthalimidyl) | C$_6$H$_5$— | H | H | — |
| 32 (k) | —(CH$_2$)$_2$N(CH$_3$)$_2$ | C$_6$H$_5$— | H | H | — |
| 32 (l) | —(CH$_2$)$_4$N(CH$_3$)$_2$ | C$_6$H$_5$— | H | H | — |
| 33 | —(CH$_2$)$_3$N(CH$_3$)$_2$ | C$_6$H$_5$— | H | H | — |
| 42 | —(CH$_2$)$_3$N(CH$_3$)$_2$ | 3-Cl—C$_6$H$_4$ | H | H | — |

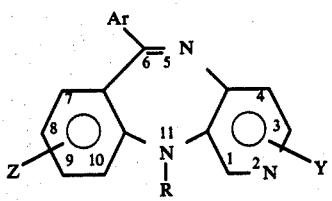

| | | | | | |
|---|---|---|---|---|---|
| 32 (d) | —(CH$_2$)$_3$N(CH$_3$)$_2$ | C$_6$H$_5$— | H | H | — |
| 32 (e) | —(CH$_2$)$_3$N(CH$_3$)$_2$ | C$_6$H$_5$— | H | 8-CH$_3$ | — |
| 32 (f) | —(CH$_2$)$_3$N(CH$_3$)$_2$ | 4-Cl—C$_6$H$_4$— | H | H | — |
| 32 (g) | —(CH$_2$)$_3$N(CH$_3$)$_2$ | C$_6$H$_5$— | H | H | — |

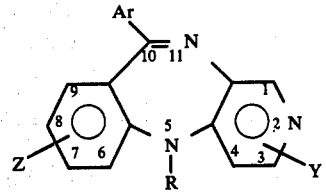

| | | | | | |
|---|---|---|---|---|---|
| 32 (h) | —(CH$_2$)$_3$N(CH$_3$)$_2$ | C$_6$H$_5$— | H | H | — |

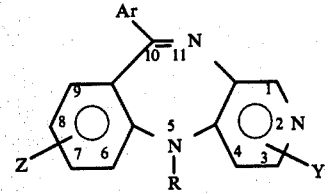

| | | | | | |
|---|---|---|---|---|---|
| 32 (i) | —(CH$_2$)$_3$N(CH$_3$)$_2$ | C$_6$H$_5$— | H | H | — |

FORMULATION AND ADMINISTRATION

Effective quantities of the compounds having the formula:

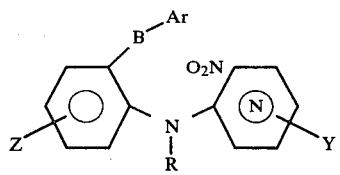

Formula Ia wherein;

R is —alk$^1$—Q;
Q is hydrogen or —NR$^1$R$^2$;
alk$^1$ is a straight or branched hydrocarbon chain containing 1–8 carbons;
B is carbonyl or thioxomethyl;
R$^1$ and R$^2$ are selected from the group consisting of hydrogen, loweralkyl, or taken together with the adjacent nitrogen atom may form a heterocyclic residue selected from 1-pyrrolidinyl, 4-morpholinyl, 1-piperidinyl, 1-piperazinyl or 4-loweralkyl-1-piperazinyl;
Ar is selected from the group consisting of 2 or 3-thienyl, 2, 3 or 4-pyridinyl, phenyl or phenyl substituted by 1 to 3 radicals selected from halo, loweralkyl, loweralkoxy, trifluoromethyl or nitro which may be the same or different;
Y is selected from the group consisting of hydrogen or 1–2 radicals selected from loweralkyl, hydroxy or loweralkoxy and may be the same or different;
Z is selected from the group consisting of hydrogen, halogen, loweralkyl, hydroxy, loweralkoxy or nitro and the pharmaceutically acceptable acid addition salts thereof.

For the parenteral administration the carrier or excipient may be a sterile, parenterally acceptable liquid; e.g. water or a parenterally acceptable oil; e.g. arachis oil contained in ampules.

Although very small quantities of the active materials of the present invention are effective when minor therapy is involved or in cases of administration to subjects having a relatively low body weight, unit dosages are usually from five milligrams or above and preferably 25, 50, or 100 milligrams or even higher, depending of course upon the emergency of the situation and the particular result desired. Five to 50 milligrams appears optimum per unit dose or usual broader ranges appear to be 1 to 500 milligrams per unit dose. Daily dosages should preferably range from 10 mg. to 100 mg. The active ingredients of the invention may be combined with other pharmacologically active agents as stated above. It is only necessary that the active ingredient constitute an effective amount; i.e. such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician.

The following formulations are representative for all of the pharmacologically active compounds of Formula Ia:

FORMULATIONS

1. Capsules

Capsules of 5 mg., 10 mg., 25 mg., and 50 mg. of active ingredient per capsule are prepared. With the higher amounts of active ingredient, reduction may be made in the amount of lactose.

| Typical blend for encapsulation | Per Capsule, mg. |
|---|---|
| Active ingredient, as salt | 5 |
| Lactose | 259 |
| Starch | 126 |
| Magnesium stearate | 4 |
| Total | 394 |

Additional capsule formulations preferably contain a higher dosage of active ingredient and are as follows:

| Ingredients | 100 mg. per Capsule | 250 mg. per Capsule | 500 mg. per Capsule |
|---|---|---|---|
| Active ingredient, as salt | 100 | 250 | 500 |
| Lactose | 209 | 163 | 95 |
| Starch | 87 | 81 | 47 |
| Magnesium stearate | 4 | 6 | 8 |
| Total | 400 | 500 | 650 |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

| | Per Tablet, mg. |
|---|---|
| 1. Active ingredient | 5.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 201.0 |

Uniformly blend 1, 2, 4 and 5. Prepare 3 as a 10 percent paste in water. Granulate the blend with starch paste and pass the wet mass through an 8 mesh screen. The wet granulation is dried and sized through a 12 mesh screen. The dried granules are blended with the calcium stearate and compressed.

| 3. Injectable - 2% sterile solution | Per cc |
|---|---|
| Active ingredient   mg. | 20 |
| Preservative, e.g., chlorobutanol, wt./vol. percent | 0.5 |
| Water for injection q.s. | |

Prepare solution, clarify by filtration, fill into vials, seals and autoclave.

Various modifications and equivalents will be apparent to one skilled in the art and may be made in the compounds, compositions and methods of the present invention without departing from the spirit or scope thereof, and it is therefore understood that the invention is to be limited only by the scope of the appended claims.

What is claimed is:

1. A compound selected from the group having the formula:

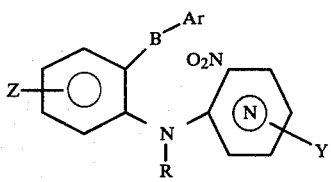

wherein;

R is hydrogen or —alk$^1$—Q;

Q is selected from hydrogen, —NR$^1$R$^2$ or halogen;

alk$^1$ is a straight or branched hydrocarbon chain containing 1-8 carbon atoms;

B is selected from carbonyl, thioxomethyl;

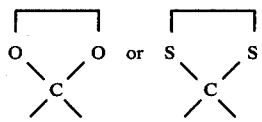

R$^1$ and R$^2$ are selected from the group consisting of hydrogen, loweralkyl, and —C(O)—O—loweralkyl;

Ar is selected from the group consisting of phenyl or phenyl substituted by 1 to 3 radicals selected from halo, loweralkyl, loweralkoxy, trifluoromethyl or nitro which may be the same or different;

Y is selected from the group consisting of hydrogen, or 1-2 radicals selected from loweralkyl, hydroxy or loweralkoxy and may be the same or different;

Z is selected from the group consisting of hydrogen, halogen, loweralkyl, hydroxy, loweralkoxy or nitro or a pharmaceutically acceptable acid addition salt thereof.

2. The compound of claim 1 which is [2-[(3-nitro-2-pyridinyl)amino]phenyl]phenylmethanone.

3. The compound of claim 1 which is [2-[(3-nitro-2-pyridinyl)amino]phenyl]phenylmethanone hydrochloride.

4. The compound of claim 1 which is 3-chlorophenyl[2-[(3-nitro-2-pyridinyl)amino]phenyl]methanone.

5. The compound of claim 1 which is [2-[[3-(dimethylamino)propyl](3-nitro-2-pyridinyl)amino]phenyl]phenylmethanone.

6. The compound of claim 1 which is 3-chlorophenyl[2-[[3-dimethylamino)propyl](3-nitro-2-pyridinyl)amino]phenyl]methanone.

7. The compound of claim 1 which is (2-chlorophenyl)[2-[(3-nitro-2-pyridinyl)amino]phenyl]methanone.

8. The compound of claim 1 which is (4-chlorophenyl)[2-[(3-nitro-2-pyridinyl)amino]phenyl]methanone.

9. The compound of claim 1 which is (3-fluorophenyl)[2-[(3-nitro-2-pyridinyl)amino]phenyl]methanone.

10. The compound of claim 1 which is (3-fluorophenyl)[2-[methyl(3-nitro-2-pyridinyl)amino]phenyl]methanone.

* * * * *